United States Patent
Michaels et al.

(10) Patent No.: US 9,884,039 B2
(45) Date of Patent: Feb. 6, 2018

(54) PHARMACEUTICAL FORMULATIONS FOR SUBCUTANEOUS ADMINISTRATION OF FUROSEMIDE

(71) Applicant: scPharmaceuticals Inc., Lexington, MA (US)

(72) Inventors: Scott A. Michaels, Lexington, MA (US); Pieter Muntendam, Lexington, MA (US); Glenn R. Larsen, Lexington, MA (US)

(73) Assignee: scPharmaceuticals Inc., Burlington, MA (US)

( * ) Notice: Subject to any disclaimer, the term of this patent is extended or adjusted under 35 U.S.C. 154(b) by 0 days.

(21) Appl. No.: 14/781,706

(22) PCT Filed: Apr. 3, 2014

(86) PCT No.: PCT/US2014/032800
§ 371 (c)(1),
(2) Date: Oct. 1, 2015

(87) PCT Pub. No.: WO2014/165660
PCT Pub. Date: Oct. 9, 2014

(65) Prior Publication Data
US 2016/0051507 A1      Feb. 25, 2016

Related U.S. Application Data

(60) Provisional application No. 61/808,962, filed on Apr. 5, 2013.

(51) Int. Cl.
*A61K 31/341* (2006.01)
*A61K 47/18* (2017.01)
*A61K 9/00* (2006.01)
*A61K 9/08* (2006.01)
*A61K 31/635* (2006.01)
*A61K 47/02* (2006.01)

(52) U.S. Cl.
CPC .......... *A61K 31/341* (2013.01); *A61K 9/0019* (2013.01); *A61K 9/08* (2013.01); *A61K 31/635* (2013.01); *A61K 47/02* (2013.01); *A61K 47/18* (2013.01)

(58) Field of Classification Search
None
See application file for complete search history.

(56) References Cited

U.S. PATENT DOCUMENTS

| | | | |
|---|---|---|---|
| 4,663,348 A | 5/1987 | Chafetz et al. | |
| 4,698,361 A | 10/1987 | Di Schiena | |
| 5,814,623 A * | 9/1998 | Ranade | A61K 9/0019 514/155 |
| 8,282,366 B2 | 10/2012 | Hilber et al. | |
| 8,372,809 B2 | 2/2013 | Unemori et al. | |
| 8,414,532 B2 | 4/2013 | Brandt et al. | |
| 2008/0076828 A1 | 3/2008 | Dalton et al. | |
| 2009/0233951 A1* | 9/2009 | Somberg | A61K 9/0019 514/266.31 |
| 2011/0060280 A1* | 3/2011 | Caffey | A61M 5/14248 604/151 |
| 2012/0077829 A1 | 3/2012 | Somberg et al. | |
| 2013/0252932 A1 | 9/2013 | Seward | |

FOREIGN PATENT DOCUMENTS

| | | |
|---|---|---|
| EP | 0 801 950 | 10/1997 |
| EP | 1 078 636 | 2/2010 |
| WO | 92/21769 | 12/1992 |

OTHER PUBLICATIONS www.infusionnurse.org, Is there a difference? Osmolarity vs. Osmolality . . . , May 14, 2010, printed from https://infusionnurse.org/2010/05/14/osmolarity-vs-osmolality/, 3 pages.*
www.pharmacorama.com, Routes of drug administration—Parenteral route, Aug. 19, 2006, printed from http://www.pharmacorama.com/en/Sections/Pharmacokinetics-5.php, 5 pages.*
Al-Obaid et al., "Analytical Profile of Furosemide," Analytical Profiles of Drug Substances, 18:153-193 (1990).
Bundgaard et al., "Photodegradation and hydrolysis of furosemide and furosemide esters in aqueous solutions," International Journal of Pharmaceutics, 42:217-224 (1988).
Cruz et al., "Kinetics and Mechanism of Hydrolysis of Furosemide," International Journal of Pharmaceutics, 2:275-281 (1979).
Devarakonda et al., "Effect of pH on the solubility and release of furosemide from polyamidoamine (PAMAM) dendrimer complexes," International Journal of Pharmaceutics, 345:142-153 (2007).
Fransson et al., "Local Tolerance of Subcutaneous Injections," J. Pharm. Pharmacol., 48:1012-1015 (1996).
Granero et al., "Biowaiver Monographs for Immediate Release Solid Oral Dosage Forms: Furosemide," Journal of Pharmaceutical Sciences, 99(6):2544-2556 (2010).
Laursen et al., "Pain Perception after Subcutaneous Injections of Media Containing Different Buffers," Basic & Clinical Pharmacology & Toxicology, 98:218-221 (2006).

(Continued)

*Primary Examiner* — Gigi Huang
(74) *Attorney, Agent, or Firm* — Goodwin Procter LLP

(57) ABSTRACT

The present teachings relate to liquid pharmaceutical formulations of furosemide, where the pharmaceutical formulations include a molar excess of tris(hydroxymethyl)aminomethane to furosemide, have a pH in the range of 7 to 8.5, and a concentration of tris(hydroxymethyl)aminomethane greater than or equal to about 50 mM. The present teachings can improve the stability of liquid pharmaceutical formulations including furosemide and the suitability of such pharmaceutical formulations for subcutaneous administration or delivery.

23 Claims, 10 Drawing Sheets

(56) References Cited

OTHER PUBLICATIONS

Ponto et al., Furosemide (Frusemide) A Pharmacokinetic/Pharmacodynamic Review (Part II), Clin. Pharmacokinet., 18:460-471 (1990).
Strickley, "Solubilizing Excipients in Oral and Injectable Formulation," Pharmaceutical Research, 21(2):201-230 (2004).
Ward et al., "Discomfort from an Alkaline Formulation Delivered Subcutaneously in Humans: Albumin at pH 7 versus pH 10," Clin Drug Investig, 32(7):433-438 (2012).
Ghanekar et al., "Stability of Furosemide in Aqueous Systems," Journal of Pharmaceutical Sciences, 67(6):808-811 (1978).
Extended European Search Report and Opinion dated Sep. 5, 2016 for European Patent Application No. 14778339.3, 10 pages.
International Search Report and Written Opinion dated Sep. 12, 2014, for International Application No. PCT/US2014/032800, 9 pages.
American Regent, Inc., Furosemide Injection, USP, Product Insert, 16 pages (Feb. 2014).
Aulton, M.E., "Aulton's Pharmaceutics: The Design and Medicines," Churchill Livingstone, 3rd Ed., (Dec. 31, 2007), Table 24.4.
Intellectual Property Office of Singapore Search Report for Application No. 11201508251R, dated Oct. 12, 2016 (2 pages).
Intellectual Property Office of Singapore Written Opinion for Application No. 11201508251R, dated Oct. 21, 2016 (5 pages).
Amendment and Request for Reconsideration including Declaration Under 37 C.F.R. 1.132 of John C. Somberg for U.S. Appl. No. 12/077,008, dated Sep. 14, 2010, which application matured into U.S. Pat. No. 7,923,447 dated Apr. 12, 2011 (14 pages).

* cited by examiner

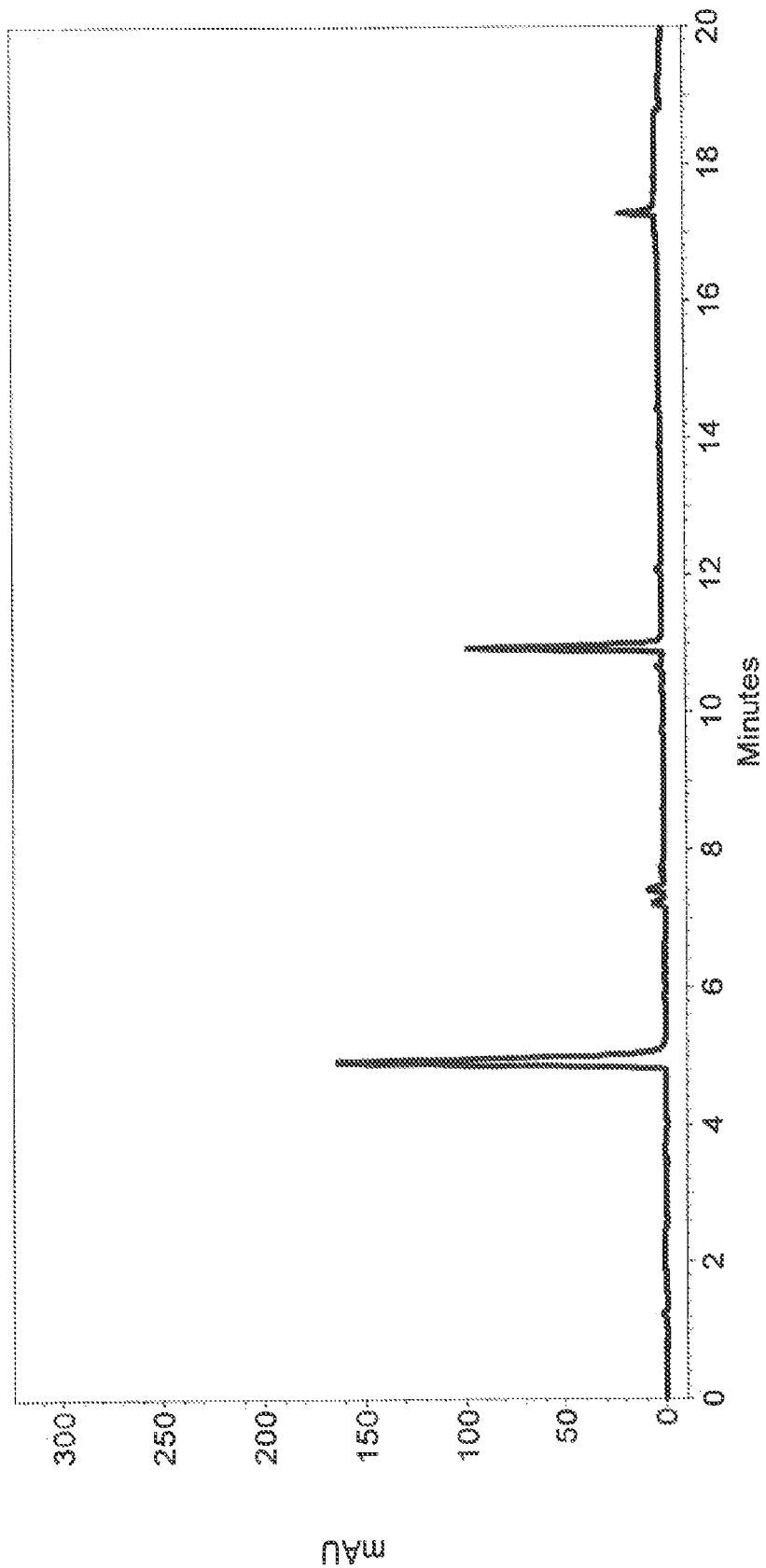

PHARMACEUTICAL FORMULATIONS FOR SUBCUTANEOUS ADMINISTRATION OF FUROSEMIDE

CROSS-REFERENCE TO RELATED APPLICATIONS

This application is a U.S. national stage application under 35 U.S.C. § 371 of International Application No, PCT/US2014/032800, filed on Apr. 3, 2014, Which claims priority to and the benefit of U.S. Patent Application No. 61/808,962, filed on Apr. 5, 2013, each of which is incorporated by reference herein in its entirety for all purposes.

FIELD

The present teachings relate to pharmaceutical formulations including furosemide. More specifically, the present teachings relate to pharmaceutical formulations including furosemide and a buffer including tris(hydroxymethyl)aminomethane.

BACKGROUND

Furosemide, an exemplary loop diuretic, can be used in the treatment of hypertension, edema and related conditions, including decompensated heart failure. Furosemide is commonly used in the treatment and/or management of edema associated with cardiac, renal, and hepatic insufficiency or failure, for example, congestive heart failure. H. Bundgaard, T. Norgaard, N. M. Nielsen, "*Photodegradation and hydrolysis of furosemide and fuirosemide esters in aqueous solutions,*" International Journal of Pharmaceutics 42, 217 (1988).

Oral bioavailability, and therefore oral efficacy, of furosemide is limited. Furosemide is commonly administered both parenterally and orally, although highly variable oral absorption is observed due to the combined effects of limited solubility and decreased stability at acidic pH. B. Devarakonda, D. P. Otto, A. Judefeind, R. A. Hill, M. M. de Villiers, "*Effect of pH on the solubility and release of furosemide from polyamidoamine (PAMAM) dendrimer complexes,*" International Journal of Pharmaceutics 345, 142 (Dec. 10, 2007). Accordingly, furosemide typically is administered intravenously or intramuscularly for most patients with decompensated heart failure or other forms of more advanced edema.

Intravenous administration of a pharmaceutical drug, such as furosemide, requires a trained healthcare professional for placement of the catheter and administration of the drug solution. In contrast, subcutaneous administration of a pharmaceutical drug can be accomplished with the aid of auto-injection devices and/or minipumps or subcutaneous injections or infusions, which can permit administration to be performed by the patient or caregiver, for example, at home. Subcutaneous administration of furosemide by the patient or caregiver also can allow for more optimal therapeutic administration and total dose to provide a more appropriate pharmacokinetic and pharmacodynamic profile and patient outcome.

For subcutaneous administration, discomfort and pain during administration should be minimized so as to avoid poor patient compliance with the treatment regimen. Factors that can contribute to pain and discomfort perceived by a patient upon, during, or after subcutaneous administration include the injection volume, the pH of the formulation, and the osmoticity or tonicity of the formulation. Moreover, such a formulation should be stable in solution so that it readily is available for use and/or can be pre-loaded into a variety of dispensing devices.

Therefore, a need exists for improved pharmaceutical formulations containing furosemide that are stable in solution, contain a sufficient concentration of furosemide, and are at an appropriate pH and osmolality, for example, to permit subcutaneous administration of furosemide.

SUMMARY

It has now been discovered that a stable, liquid pharmaceutical formulation including furosemide can be realized by including a molar excess of tris(hydroxymethyl)aminomethane ("Tris") to furosemide, where the concentration of Tris in the pharmaceutical formulation is greater than or equal to about 50 mM and the pH of the pharmaceutical formulation is between about 7 to about 8.5. The pharmaceutical formulations also can be isosmotic. Consequently, a stable, liquid pharmaceutical formulation results that can be appropriate for subcutaneous delivery of furosemide. Subcutaneous administration of furosemide can improve the cost-effectiveness, convenience, and/or patient outcomes when compared to intravenous administration.

Accordingly, the present teachings relate to pharmaceutical formulations that include furosemide and Tris as well as to the administration of such pharmaceutical formulations. The present teachings generally can improve the pH stability and/or the active pharmaceutical ingredient ("API") stability of the pharmaceutical formulations, and/or the suitability of the pharmaceutical formulations for subcutaneous administration or delivery.

Thus, in one aspect, the present teachings provide methods for treating a patient with edema or hypertension, which can be due to congestive heart failure, or renal or hepatic insufficiency or failure. The methods generally include administering to a patient a pharmaceutical formulation of the present teachings, where the pharmaceutical formulation includes furosemide, or a pharmaceutically acceptable salt, hydrate or ester thereof; and a pharmaceutically acceptable buffer including Tris, where the concentration of Tris in the pharmaceutical formulation can be greater than or equal to about 50 mM, and the pharmaceutical formulation has a molar excess of Tris to furosemide and a pH in the range of about 7 to about 8.5. In various embodiments, the pharmaceutical formulation can be isosmotic.

In particular embodiments, methods of treating a patient with or exhibiting the symptoms of edema, hypertension or heart failure can include administering subcutaneously to a patient using a patch device a pharmaceutical formulation including between about 6 mg/mL to about 10 mg/mL, of furosemide, or a pharmaceutically acceptable salt, hydrate or ester thereof; and a pharmaceutically acceptable buffer comprising Tris, where the concentration of Tris in the pharmaceutical formulation is greater than or equal to about 50 mM; and where the molar ratio of Tris to furosemide is greater than or equal to 1.65, and the pharmaceutical formulation has a pH between about 7.2 to about 8 and is isosmotic.

In another aspect, the present teachings provide pharmaceutical formulations including furosemide, or pharmaceutically acceptable salt, hydrate or ester thereof; and a pharmaceutically acceptable buffer including Tris in an amount greater than or equal to about 50 mM, where the molar ratio of Tris to furosemide is greater than one and the pharmaceutical formulation can have a pH in the range of about 7 to about 8.5 and can be isosmotic.

The foregoing as well as other features and advantages of the present teachings will be more fully understood from the following figures, description, examples, and claims.

DESCRIPTION OF DRAWINGS

It should be understood that the drawings described below are for illustration purposes only. The drawings are not necessarily to scale, with emphasis generally being placed upon illustrating the principles of the present teachings. The drawings are not intended to limit the scope of the present teachings in any way.

FIGS. 4A-4C are HPLC chromatograms of samples of 8 mg/mL furosemide in 25 mM Tris-buffered, isosmotic solutions at pH's 8, 7.4, and 7, respectively, stored at 70° C. for three months.

DETAILED DESCRIPTION

Figure 1:
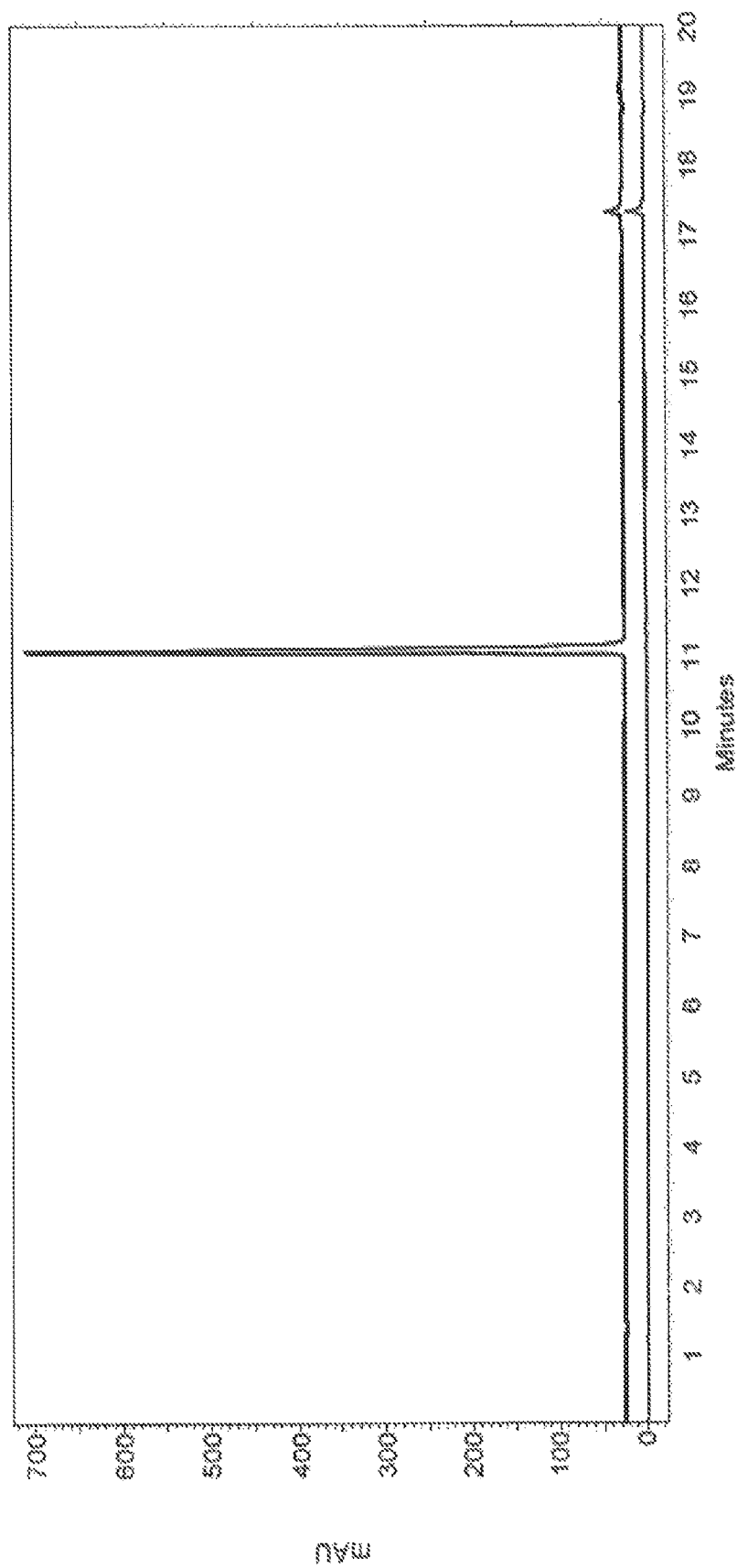
FIG. 1 is a representative high pressure liquid chromatography ("HPLC") chromatogram of samples of 8 mg/mL furosemide in 50 mM Tris-buffered, isosmotic solutions at pH's 8, 7.4, and 7 stored at −20° C., 2° C.-8° C., 25° C., and 40° C. for three months, where the upper trace shows the retention time of furosemide at about 11 minutes and the lower trace is a diluent blank.
Figure 2A:
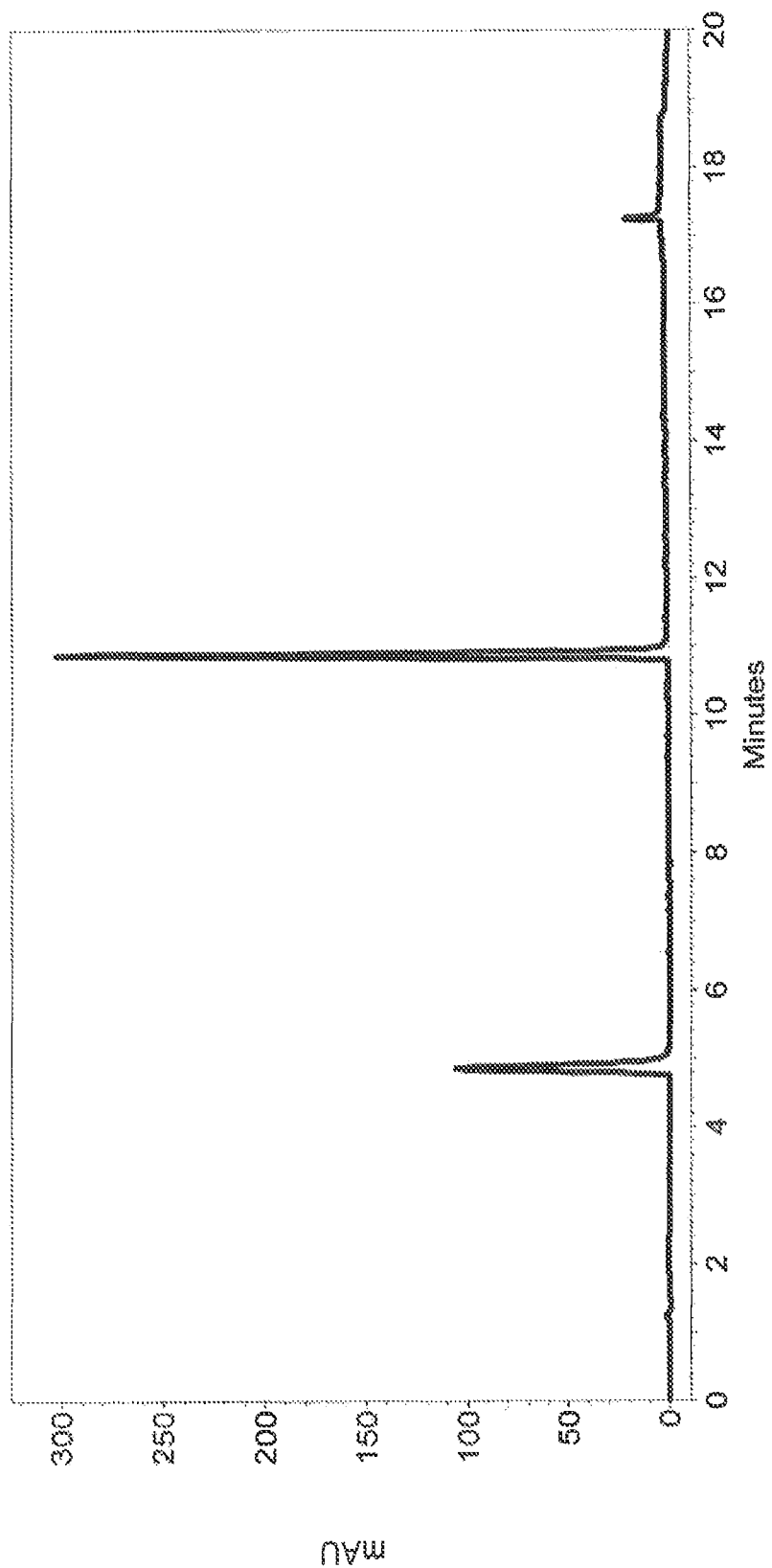
FIGS. 2A-2C are HPLC chromatograms of samples of 8 mg/mL furosemide in 100 mM Tris-buffered, isosmotic solutions at pH's 8, 7.4, and 7, respectively, stored at 70° C. for three months.
Figure 2B:
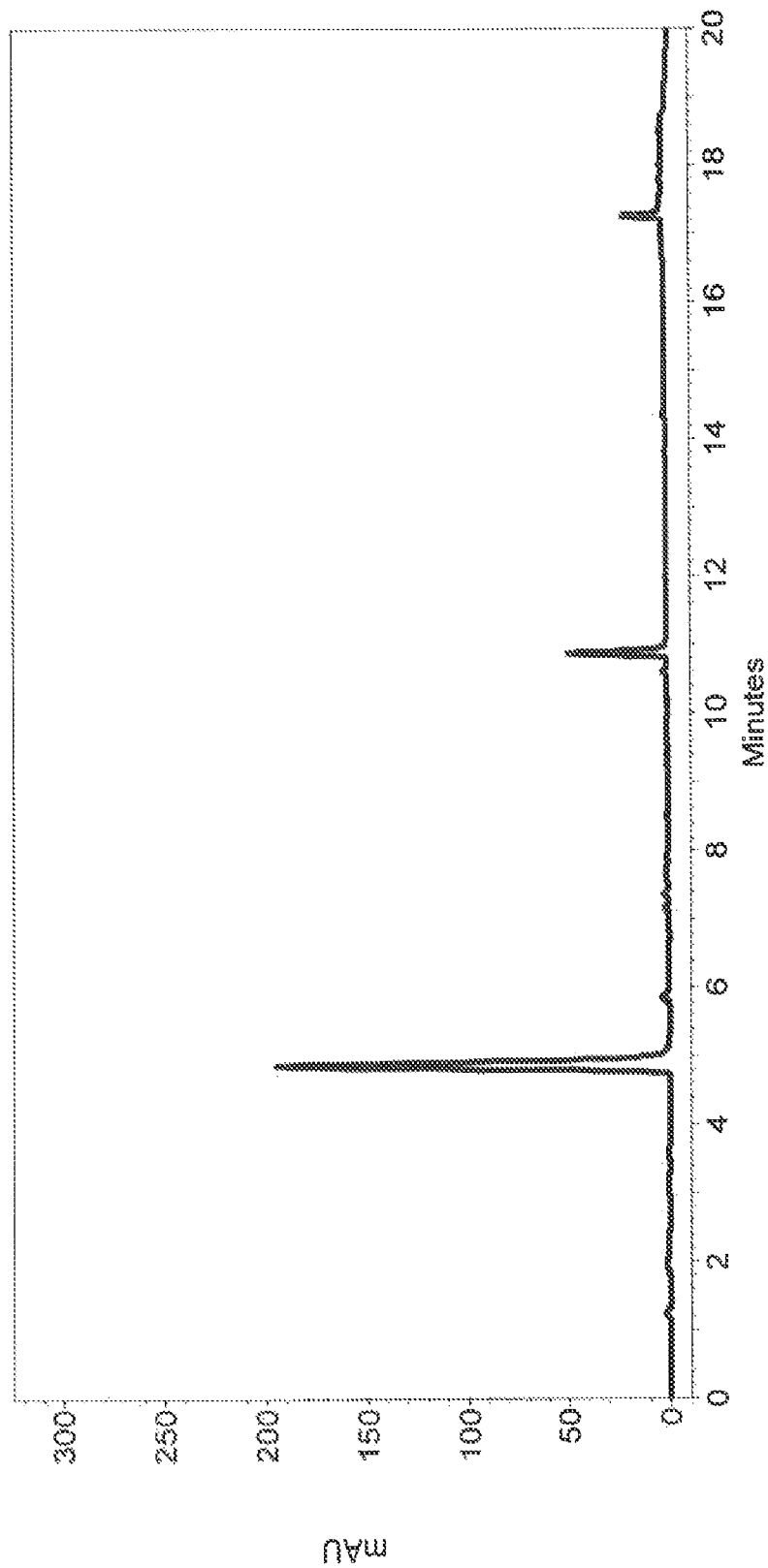
Figure 2C:
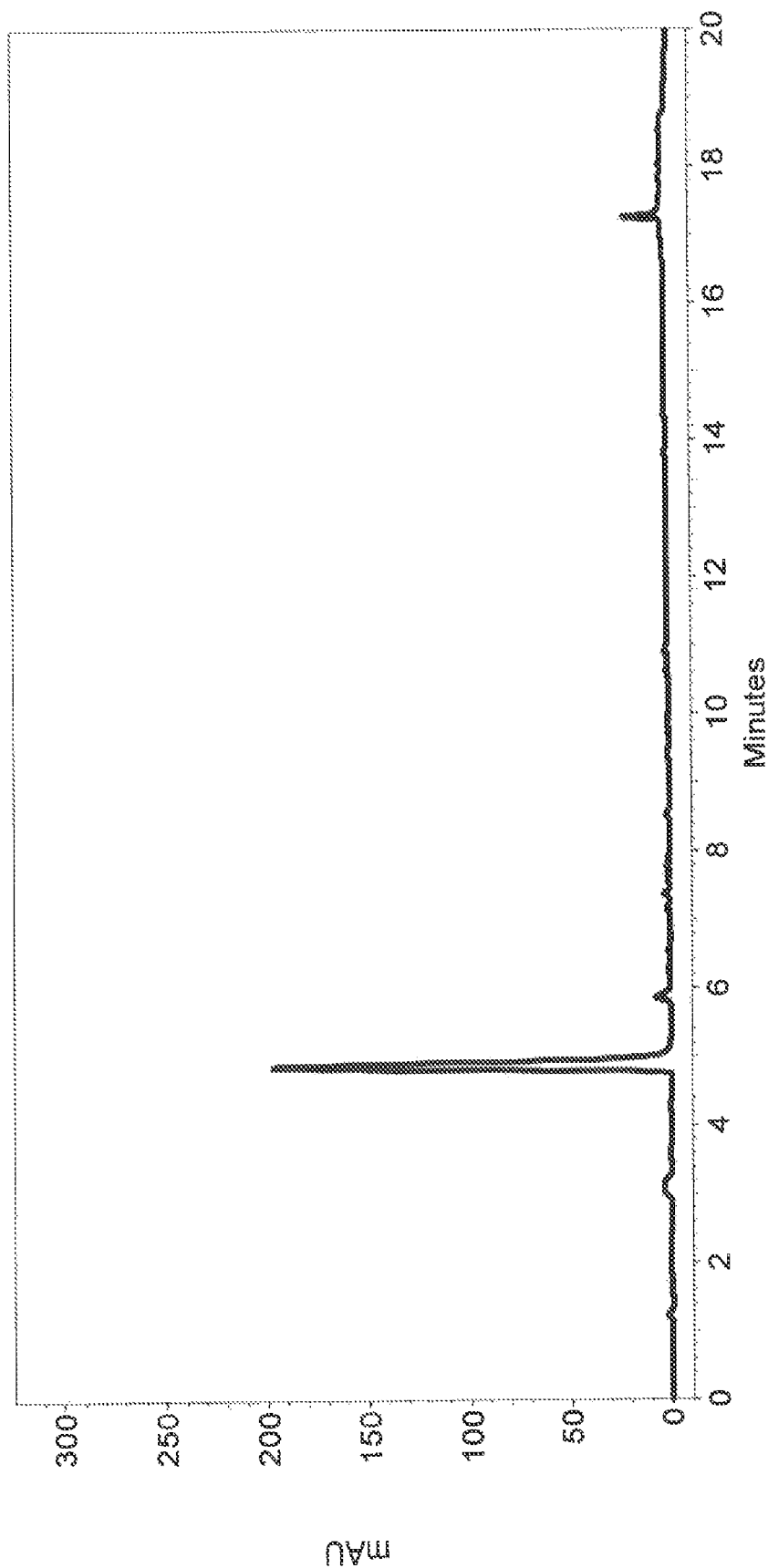
Figure 3A:
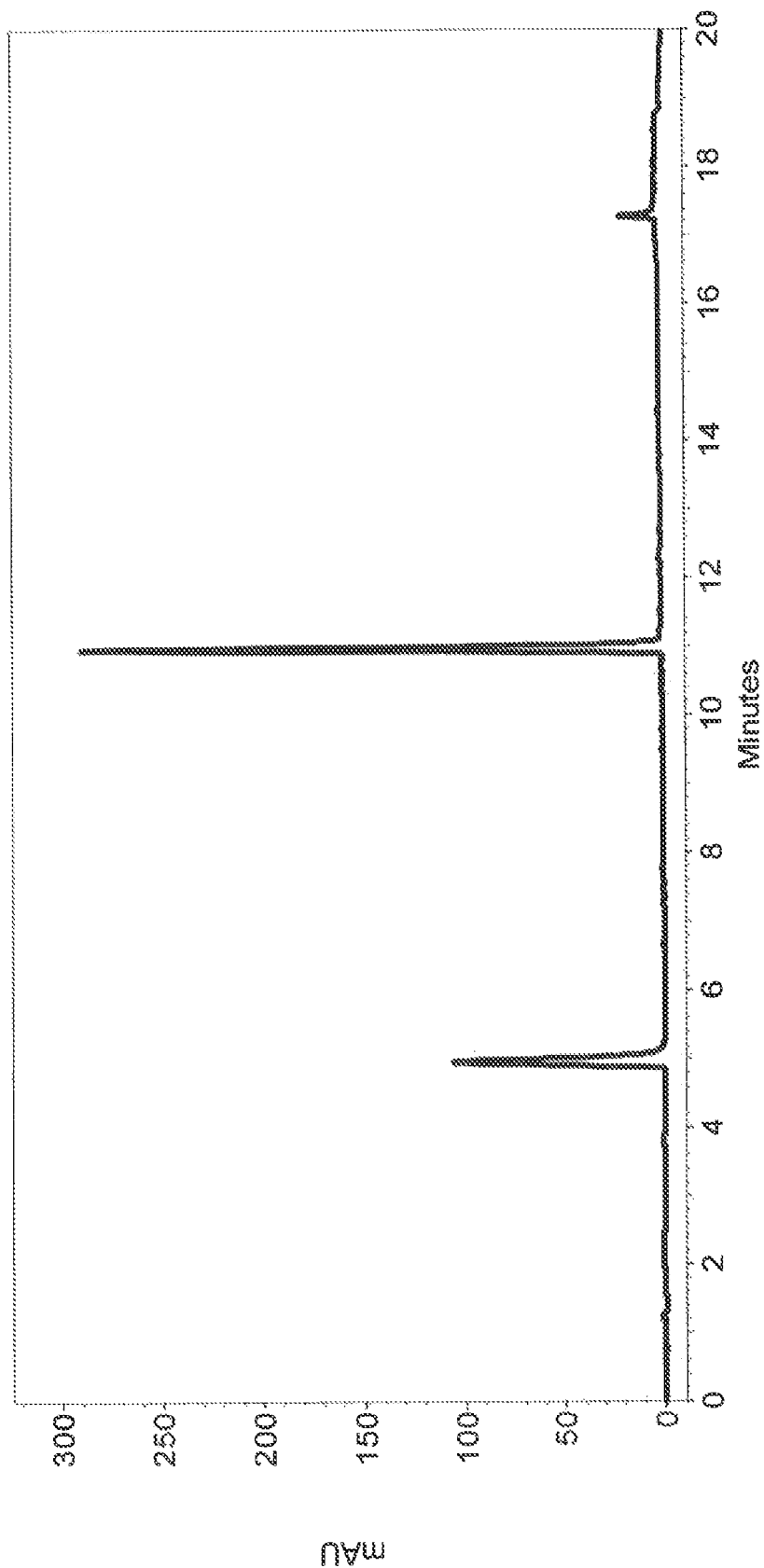
FIGS. 3A-3C are HPLC chromatograms of samples of 8 mg/mL furosemide in 50 mM Tris-buffered, isosmotic solutions at pH's 8, 7.4, and 7, respectively, stored at 70° C. for three months.
Figure 3B:
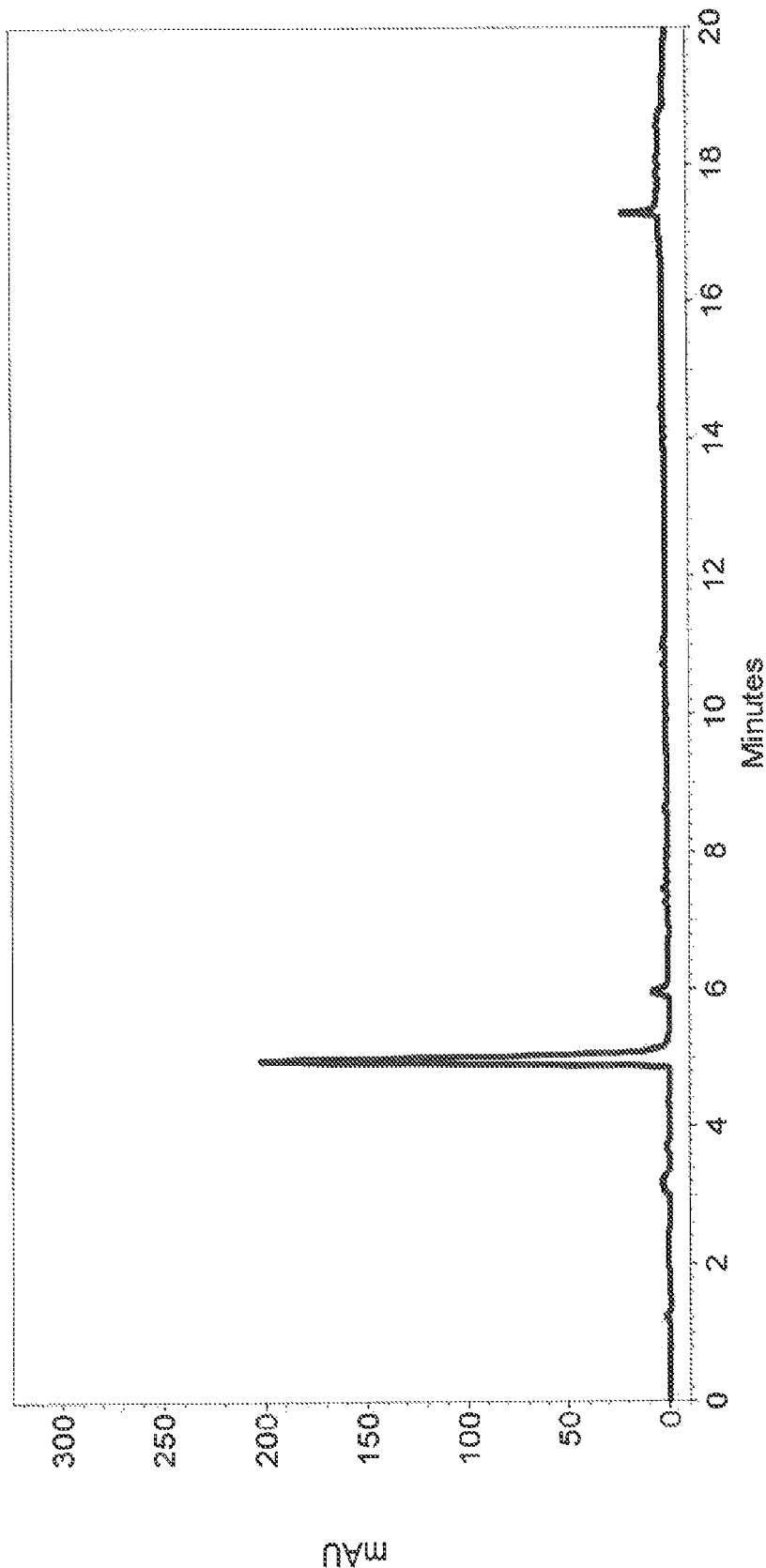
Figure 3C:
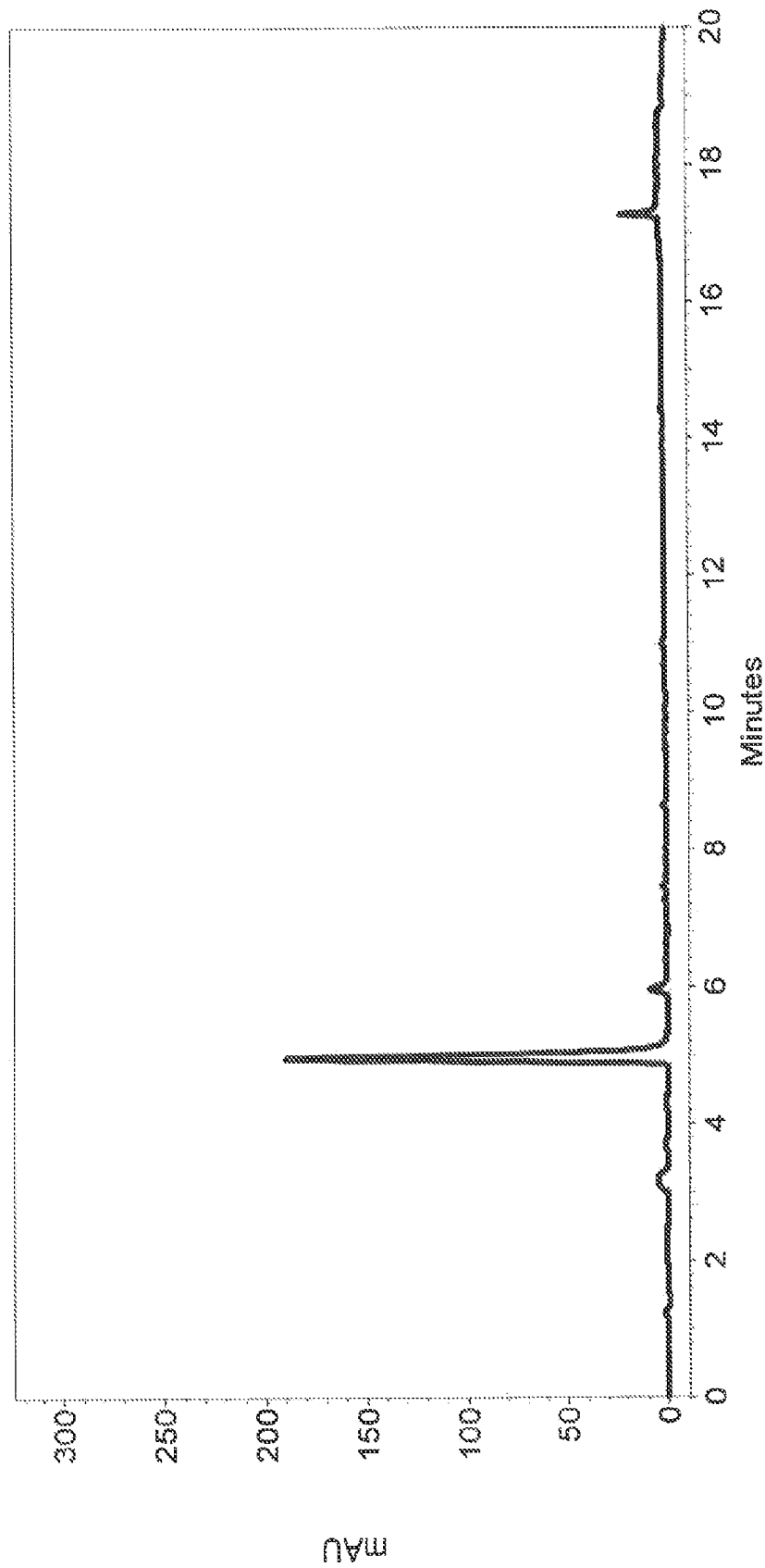
Figure 4B:
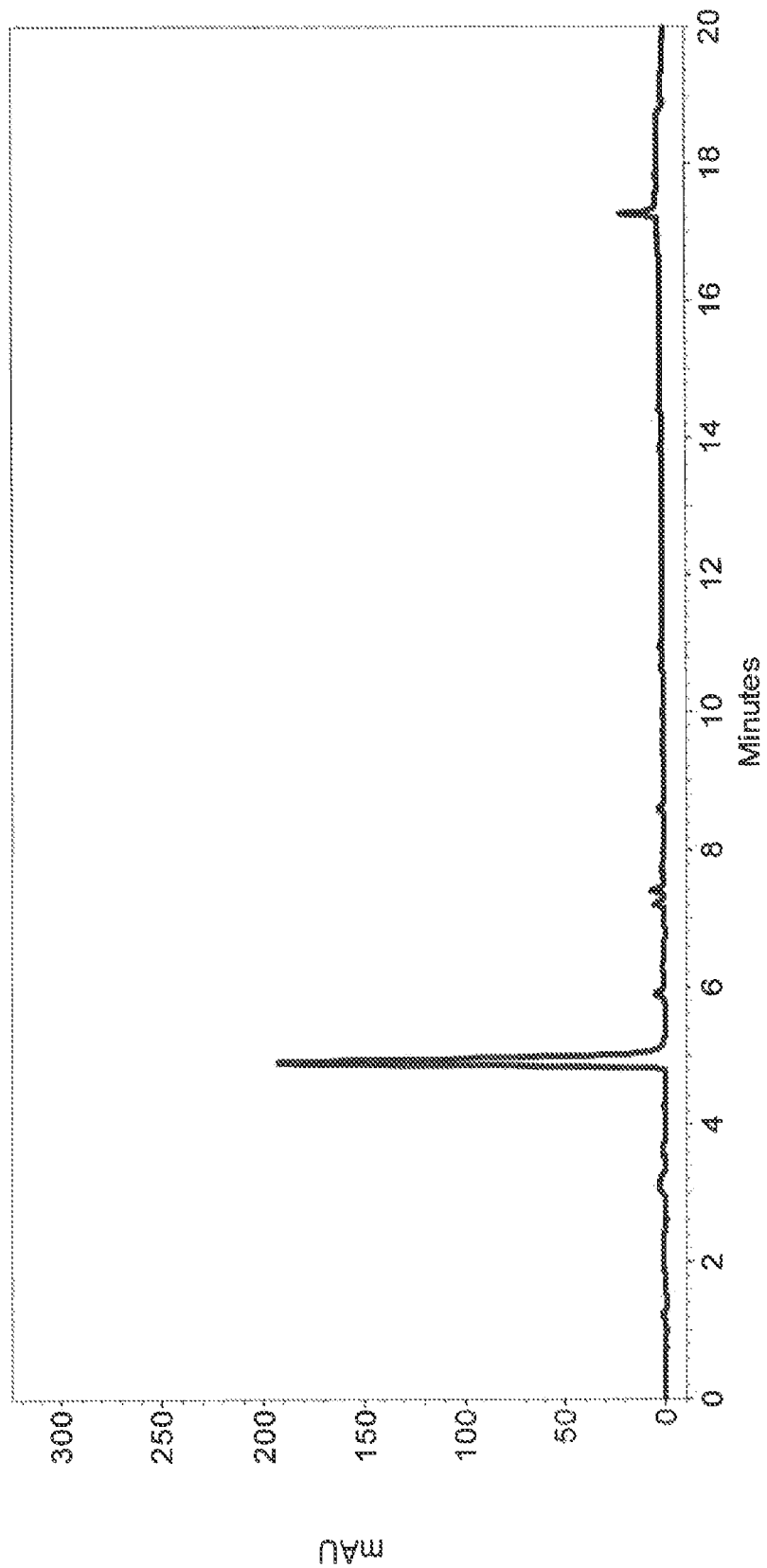
Figure 4C:
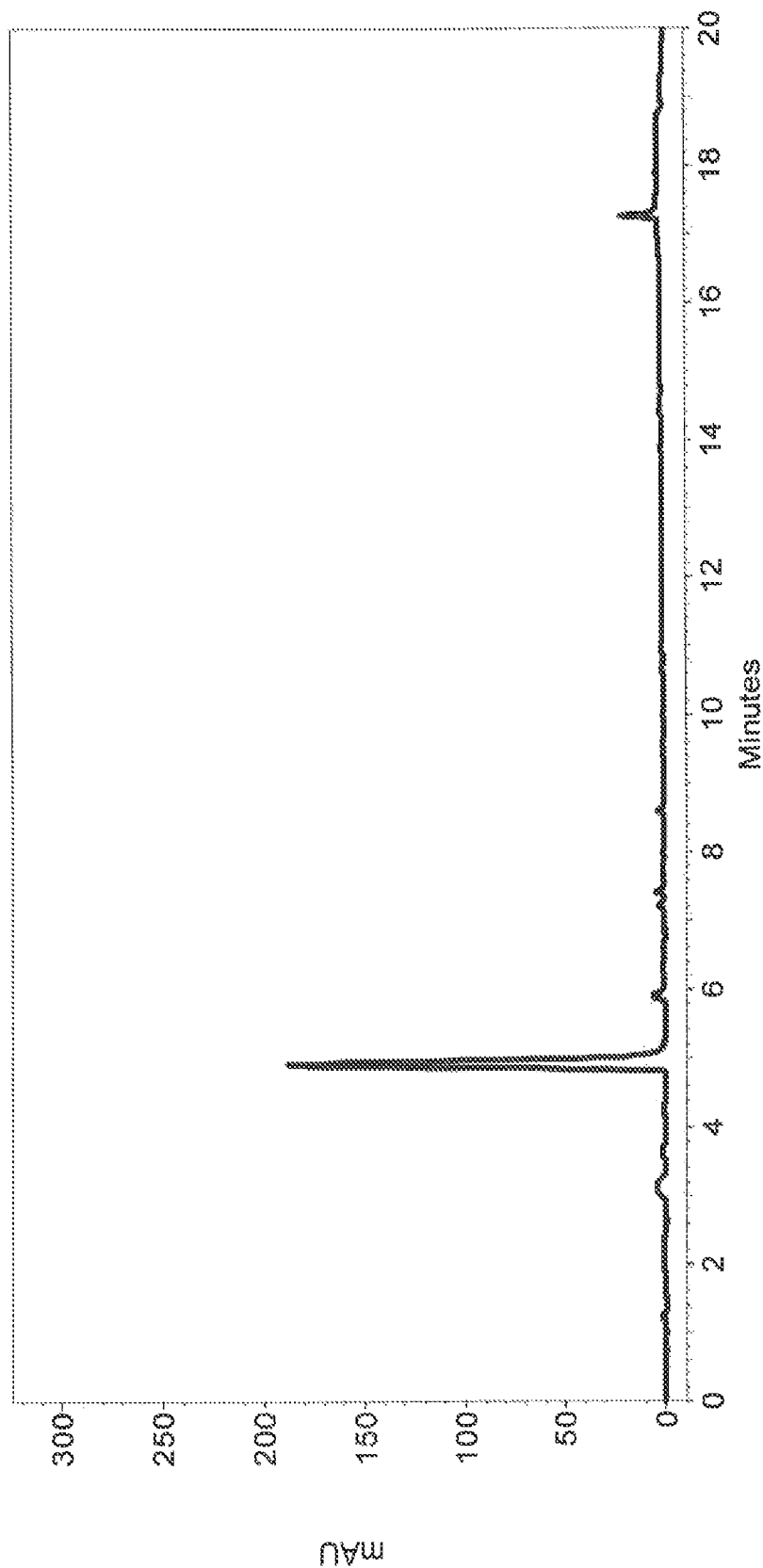

The present teachings can enable the subcutaneous administration of furosemide. More specifically, the present teachings provide methods that use and liquid compositions (liquid pharmaceutical formulations) that include furosemide and a buffer including tris(hydroxymethyl)aminomethane ("Tris"). Such methods and pharmaceutical formulations can be useful in the treatment of edema, hypertension or heart failure in a patient having or exhibiting symptoms of such conditions.

For subcutaneous administration, as with any type of drug administration, pain and discomfort during administration should be minimized. To that end, the injection volume (relating to the concentration of the API in the formulation), the pH, and the osmoticity or tonicity of the formulation should be controlled to provide a liquid formulation that will assist in patient compliance with the treatment regimen. In addition, a useful pharmaceutical formulation for subcutaneous administration should be a stable, liquid pharmaceutical formulation so that it can be stored and available for use without any preparation, particularly if the pharmaceutical formulation is to be dispensed from a micropump, a patch device, or other pre-loaded device.

Accordingly, a pharmaceutical formulation should have a sufficient concentration of API so as to minimize the volume of formulation that needs to be administered subcutaneously to provide a therapeutically effective amount of the drug. A pharmaceutical formulation for subcutaneous administration should have a pH at about or at physiological pH, or be within a relatively narrow range of pH's near physiological pH (e.g., between 6 or 6.5 to about 8.5) so that the administered formulation readily can equilibrate to physiological pH. In addition, the pharmaceutical formulation should be substantially isosmotic or isotonic. Moreover, the pharmaceutical formulation should be API and/or pH stable over a sufficient time so that the formulation has a reasonable shelf life and readily can be available for use when needed.

As discussed herein, furosemide has poor water solubility. The intrinsic aqueous solubility of furosemide at room temperature has been reported to about 18.25 micrograms per milliliter ("μg/mL"). G. E. Granero et al., "*Biowaiver monographs for immediate release solid oral dosage forms: furosemide,*" *Journal of Pharmaceutical Sciences* 99, 2544 (June 2010). Consequently, furosemide typically requires an alkaline environment for adequate solubility and stability. The commercial formulation for injectable furosemide contains 10 mg/mL of furosemide in a saline solution adjusted to pH 8.0-9.3 with sodium hydroxide or hydrochloric acid, as necessary. I. American Reagent, Furosemide Injection, USP. Product Insert. However, such a high pH is inappropriate for subcutaneous administration.

U.S. Pat. No. 4,698,361 to Di Schiena (the "'361 patent") describes the tris(hydroxymethyl)aminomethane salt of furosemide as being highly soluble in water and having a pH between 6-6.5. The '361 patent describes making the salt using a 1:1 molar ratio of furosemide to tris(hydroxymethyl) aminomethane and using the salt in pharmaceutical forms for injection (e.g., intramuscular and intravenous) and for oral administration. The '361 patent further describes isolating the salt or disposing a solution preparation of the salt in vials suitable for injection.

However, it now has been discovered that a stable, liquid pharmaceutical formulation containing furosemide that can achieve one or more of the above criteria desired for subcutaneous administration can be realized by including a molar excess of Tris to furosemide in the pharmaceutical formulation, where the pharmaceutical formulation includes a concentration of Tris greater than or equal to about 50 mM and has a pH between about 7 to about 8.5. In particular, the pharmaceutical formulations of the present teachings include furosemide and a buffer including Tris, where the pharmaceutical formulation has a pH range between about 7 and about 8.5, the concentration of Tris in the pharmaceutical formulation is greater than or equal to about 50 mM, and the molar ratio of Tris to furosemide is greater than one. In various embodiments, the pharmaceutical formulation can be isosmotic.

In certain embodiments, the pharmaceutical formulation can have a pH in the range of about 7.2 to about 8, about 7.2 to about 7.8, or about 7.2 to about 7.6. In particular embodiments, the pharmaceutical formulations can have a pH in the range of about 7.3 to about 8, about 7.3 to about 7.8, about 7.3 to about 7.6, or about 7.3 to about 7.5. In some embodiments, the pharmaceutical formulation can have a pH in the range of about 7.4 to about 8, about 7.4 to about 7.8, or about 7.4 to 7.6.

In various embodiments, the molar ratio of Tris to furosemide in the pharmaceutical formulation can be greater than about 1.5, or greater than about 1.65, or greater than about two, or greater than about 2.5, or greater than about three. In particular embodiments, the molar ratio of Tris to furosemide can be greater than about 3.5, or more.

Further, in various embodiments, the Tris in the pharmaceutical formulation can be greater than or equal to about 100 mM. In some embodiments, the concentration of Tris can be greater than or equal to about 150 mM, greater than or equal to about 200 mM, or greater than or equal to about 250 mM. In certain embodiments, the concentration of Tris can be in a range of about 50 mM to about 500 mM, about 50 mM to about 250 mM, about 50 mM to about 150 mM, or about 50 mM to about 100 mM. In particular embodiments, the concentration of Tris can be about 50 mM or about 100 mM.

In various embodiments, the pharmaceutical formulation can be isosmotic. In some embodiments, the pharmaceutical formulation can have an osmolality of between about 250 mOsM (or 250 mOsm/kg) to about 350 mOsM (or 350 mOsm/kg), about 275 mOsM (or 275 mOsm/kg) to about 325 mOsM (or 325 mOsm/kg), or about 290 mOsM (or 290 mOsm/kg) to about 310 mOsM (or 310 mOsm/kg).

In addition, the pharmaceutical formulations of the present teachings can achieve a level of solubility of furosemide that is suitable for subcutaneous administration. For example, the amount of furosemide in a pharmaceutical formulation can be about 5 mg/mL or greater, about 8 mg/mL or greater, or about 10 mg/mL or greater. In various embodiments, the amount of furosemide can be about 15 mg/mL or greater, about 20 mg/mL or greater, about 25 mg/mL or greater, or about 30 mg/mL or greater.

Some embodiments, furosemide can be present in an amount between about 2 mg/mL to about 20 mg/mL, between about 2 mg/mL to about 15 mg/mL, between about 2 mg/mL to about 10 mg/mL, between about 6 mg/mL to about 10 mg/mL, or between about 6 mg/mL to about 15 mg/mL. In some embodiments, furosemide can be present in an amount about 6 mg/mL, about 8 mg/mL, about 10 mg/mL, about 12 mg/mL, about 15 mg/mL, about 20 mg/mL, or about 30 mg/mL.

Moreover, in various methods and compositions of the present teachings, the pharmaceutical formulation can be substantially pH stable and/or API stable at room temperature for at least three months, or for at least one year. In some embodiments, the pharmaceutical formulation can be substantially pH stable and/or API stable at room temperature for at least two years, for at least three years, or more. In certain embodiments, the pharmaceutical formulations of the present teachings can exhibit an increased API stability and/or an increased pH stability at room temperature for one year and/or two years compared to a substantially identical pharmaceutical formulation but for the molar ratio of Tris to furosemide being about 1:1.

In particular embodiments, the pharmaceutical formulations of the present teachings can exhibit an increased pH stability and/or an increased API stability when exposed to a temperature of about 70° C. for three months compared to a substantially identical pharmaceutical formulation but for the molar ratio of Tris to furosemide being about 1:1.

In some embodiments, the pharmaceutical formulations of the present teachings can exhibit an increased API stability when exposed to light, for example, sunlight and/or white light, compared to a substantially identical pharmaceutical formulation but for the molar ratio of Tris to furosemide being about 1:1. In various embodiments, the pharmaceutical formulations can exhibit an increased API stability under termination sterilization conditions, for example, dry heat sterilization, compared to a substantially identical pharmaceutical formulation but for the molar ratio of Tris to furosemide being about 1:1.

In various embodiments, the pharmaceutical formulation is administered subcutaneously, for example, using a pump device such as a micropump or a patch device. However, in certain embodiments, the pharmaceutical formulation can be administered intravenously. Administering intravenously the pharmaceutical formulations of the present teachings can provide certain benefits as the pharmaceutical formulations can be at or near physiological pH and/or can be isosmotic as well as can include an increased concentration of furosemide.

Throughout the application, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise.

Where the use of the term "about" is before a quantitative value, the present teachings also include the specific quantitative value itself, unless specifically stated otherwise. As used herein, the term "about" refers to a ±10% variation from the nominal value unless otherwise indicated or inferred. For example, in certain applications, such as pH measurements, the term "about" can refer to a ±5%, or a ±2.5%, or a ±1% variation from the nominal value or a fixed variation from the nominal value, for example, ±0.1 pH units or ±0.2 pH units.

It should be understood that the order of steps or order for performing certain actions is immaterial so long as the present teachings remain operable. Moreover, two or more steps or actions may be conducted simultaneously.

At various places in the present specification, values are disclosed in groups or in ranges. It is specifically intended that the description include each and every individual sub-combination of the members of such groups and ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

As used herein, "patient" refers to a mammal, such as a human.

As used herein, a "compound" (including a specifically named compound, e.g., furosemide) refers to the compound itself and its pharmaceutically acceptable salts such as a sodium salt or a quaternary ammonium salt, hydrates and esters, unless otherwise understood from the context of the description or expressly limited to one particular form of the compound, i.e., the compound itself, or a pharmaceutically acceptable salt, hydrate or ester thereof. Where reference is made herein to an "API," the API can be furosemide.

As used herein, "furosemide" refers to a compound having the formula:

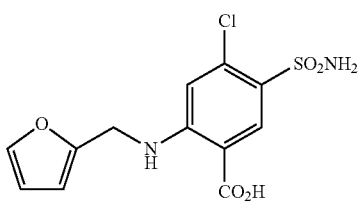 [SMILES: NS(=O)(=O)c1cc(C(=O)O)c(NCc2ccco2)cc1Cl]

and pharmaceutically acceptable salts, hydrates and esters thereof, for example, furosemide sodium salt and furosemide quaternary ammonium salt. Furosemide can be referred to by other names, for example, frusemide, 5-(aminosulphonyl)-4-chloro-2-[(2-furanyl-methyl)amino] benzoic acid, or its IUPAC name, 4-chloro-2-(furan-2-ylmethylamino)-5-sulfamoyl-benzoic acid, or its common trade name, Lasix®.

As used herein, a "buffer" refers to an aqueous solution that is resistant to changes in pH. A buffer can include a weak acid and its salt, or a weak base and its salt, which assist in maintaining the stability of the pH. Examples of buffers used in pharmaceutical formulations include bicarbonate buffers, carbonate buffers, citrate buffers, histidine buffers, phosphate buffers, tartrate buffers, tris(hydroxymethyl)aminomethane (or 2-amino-2-hydroxymethyl-propane-1,3-diol [$(HOCH_2)_3CNH_2$]) buffers, and combinations thereof. Certain of these buffers are suitable for pharmaceutical formulations administered subcutaneously.

Tris(hydroxymethyl)aminomethane or a tris(hydroxymethyl)aminomethane buffer can be referred to as "TRIS," "Tris," "Tris base," "Tris buffer," "Trisamine," "THAM," and other names. In addition, many buffers and/or buffer systems include Tris. For example, Tris-buffered saline ("TBS"), Tris-hydrochloride buffer ("Tris-HCl"), Tris base (pH 10.6), Tris/borate/ethylene diamine tetra-acetate ("EDTA") buffer ("TBE"), and Tris/acetate/EDTA buffer ("TAE"). Tris base often is used with Tris-HCl to prepare Tris buffers at a desired pH. In addition, the present teachings include Tris-related compounds, for example, compounds derived from Tris or structurally-related to Tris, that can act as a buffer.

As used herein, "tonicity" refers to the ionic strength or concentration of ions in a solution such as a pharmaceutical formulation. Tonicity often is measured in molarity ("M"). As used herein, an "isotonic solution," an "isotonic formulation," an "isotonic pharmaceutical formulation," and a pharmaceutical formulation that is "isotonic" refers to a solution or formulation that has the same or similar concentration of ions as found in bodily fluids.

As used herein, "osmoticity" and "osmolality" refer to the osmotic pressure of a solution such as a pharmaceutical formulation. Osmoticity often is measured in osmolarity ("Osm/L" or "OsM") or osmolality ("Osm/kg"), which can be used interchangeably herein. When measuring freezing point depression, the observed value is the osmolality of the solution. In contrast to tonicity, osmoticity accounts for un-ionized solutes in a solution such that when present, the osmolarity or osmolality of the solution will be higher than its tonicity. As used herein, an "isosmotic solution," an "isosmotic formulation," an "isosmotic pharmaceutical formulation," and a pharmaceutical formulation that is "isosmotic" refers to a solution or a formulation that has the same or similar concentration of solutes as found in bodily fluids. In certain embodiments, a pharmaceutical formulation that is "isosmotic" can have an osmolarity in the range of about 275 mOsM to about 350 mOsM or when the osmolality of the formulation is in the range of about 275 mOsm/kg to about 350 mOsm/kg.

As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

As used herein, "pH stable" refers to less than or equal to about a ±0.5 pH value variation in the pH of a solution, for example, a pharmaceutical formulation, over time. In various embodiments, pH stable can refer to less than or equal to about a ±0.4 pH value variation in the pH of a solution over time. In some embodiments, pH stable can refer to less than or equal to about a ±0.3 pH value variation in the pH of a solution over time. In certain embodiments, pH stable can refer to less than or equal to about a ±0.2 pH value variation in the pH of a solution over time. In particular embodiments, pH stable can refer to less than or equal to about a ±0.1 pH value variation in the pH of a solution over time.

As used herein, "API stable" refers to less than or equal to about a ±10% variation in the amount of API, for example, furosemide, in a solution, for example, a pharmaceutical formulation, over time. In various embodiments, API stable can refer to less than or equal to about a ±7.5% variation in the amount of API in a solution over time. In some embodiments, API stable can refer to less than or equal to about a ±5% variation in the amount of API in a solution over time. In certain embodiments, API stable can refer to less than or equal to about a ±3% variation in the amount of API in a solution over time. In particular embodiments, API stable can refer to less than or equal to about a ±2% variation, or a ±1% variation, in the amount of API in a solution over time.

As used herein, "physiological pH" refers to a pH of about 7.4.

As used herein, "therapeutic combination" refers to a combination of one or more active drug substances, i.e., compounds having a therapeutic utility. Typically, each such compound in the therapeutic combinations of the present teachings can be present in a pharmaceutical formulation comprising that compound and a pharmaceutically acceptable carrier. The compounds in a therapeutic combination of the present teachings can be administered simultaneously, together or separately, or separately at different times, as part of a regimen.

The present teachings provide pharmaceutical formulations that include furosemide or a therapeutic combination including furosemide, and one or more pharmaceutically acceptable carriers, excipients, or diluents such as a buffer. Examples of such carriers are well known to those skilled in the art and can be prepared in accordance with acceptable pharmaceutical procedures, such as, for example, those described in *Remington: The Science and Practice of Pharmacy*, 20th edition, ed. Alfonso R. Gennaro (Lippincott Williams & Wilkins, Baltimore, Md. (2000)). For example, liquid media or liquid carriers (which are used interchangeably herein) can be used in preparing pharmaceutical formulations of the present teachings such as solutions, suspensions, and emulsions. A compound described herein can be dissolved or suspended in a pharmaceutically acceptable liquid carrier such as a buffer, which liquid carrier also can include an organic solvent, and/or pharmaceutically acceptable oils and/or fats.

The pharmaceutical formulations of the present teachings can include other suitable pharmaceutical additives such as solubilizers, emulsifiers, buffers, preservatives, sweeteners, flavoring agents, suspending agents, thickening agents, colors, viscosity regulators, stabilizers, and osmo-regulators. Because the present teachings provide pharmaceutical formulations and their intended use is with patients such as humans, each of the ingredients or compounds of a pharmaceutical formulation described herein can be a pharmaceutically acceptable ingredient or compound.

As described herein, the present teachings provide methods and stable, liquid pharmaceutical formulations containing furosemide that can achieve one or more of the following beneficial characteristics for subcutaneous delivery. That is, the pharmaceutical formulations can be near or at physiological pH or at a pH that readily can equilibrate to physiological pH upon administration to a patient. The pharmaceutical formulations can be isosmotic and or substantially isosmotic, and can include an increased concentration of furosemide so that less volume of the liquid formulation needs to be administered per dose. The pharmaceutical formulations also can be pH stable and API stable.

A study was undertaken to determine whether a commercial formulation of furosemide for intravenous administration could be adapted for subcutaneous administration generally in view of the above beneficial characteristics.

More specifically, to confirm the insolubility and instability of furosemide in an unbuffered solution as a function of pH, a study was performed as described in Example 1. It was observed that the solution pH was strongly influenced by furosemide dissolution, such that any changes in the amount of dissolved solid affected a significant change in the solution pH. The rate of dissolution was also observed to be quite slow in neutral and weakly alkaline solutions. Highly basic (pH of 11 to 12) solution conditions were necessary to drive dissolution for concentrations as low as 0.1 mg/mL of furosemide.

Additionally, samples were prepared at both 0.1 mg/mL and 8 mg/mL furosemide and adjusted to target values in the pH range of 8 to 9 using sodium hydroxide and hydrochloric acid. The pH of these solutions was observed to be highly variable over time and as such, the solution pH was monitored for a period of 72 hours. Over this time, the solution pH was observed to continually decrease and a stable pH value was not achieved. The results suggest that an unbuffered aqueous solution of furosemide may be unstable with respect to pH when prepared below pH 9.

To confirm these preliminary observations, the reproducibility of solution behavior at pH 8.5 was evaluated for 8 mg/mL furosemide (experimental not shown). Although all samples were prepared to contain the same equivalents of furosemide, acid, and base, the observed pH values varied widely. Thus, the formulation of furosemide in an unbuffered system is likely not feasible in the pH range of 7.5 to 8.5.

As described in Example 2, a buffer was added to furosemide solutions to determine whether the pH stability of the solutions can be improved. Sodium and potassium phosphate and Tris buffer systems were evaluated at pH values in the target range of 7.0 to 8.5 and at selected buffer concentrations ranging from 150 mM to 500 mM. Buffer concentration can be an important factor when deviating from physiological pH. In such embodiments, the buffer strength can be minimized but retain its buffering capacity to permit efficient equilibration of the pharmaceutical formulation to physiological pH upon administration to a patient.

Although both phosphate and Tris buffers improved the pH stability compared to unbuffered solutions, it was discovered that the Tris buffer system maintained solution pH values closer to the nominal values than the various phosphate buffer systems evaluated. Moreover, the results unexpectedly showed that solution concentrations of up to approximately 32 mg/mL of furosemide in the target pH range could be attained.

In addition, the Tris buffer system performed better despite the significantly higher solution concentration of furosemide. That is, not only did a buffer including Tris provide a pH stable solution including furosemide, but the buffer including Tris also permitted a greater concentration of furosemide to be present in the solution, which was less alkaline and closer to physiological pH than the commercial formulations of furosemide.

Given the unexpected increase in solubility of furosemide in a buffer including Tris, the chemical stability of furosemide in buffered solutions including Tris over a pH range of 6.7 to 8.5 at ambient temperature at a solution concentration of 20 mg/mL was conducted as detailed in Example 3. No decrease in furosemide concentration was observed over 48 hours. All pH values were within 0.1 units of the initial value.

Example 4 evaluated the chemical and physical stability of furosemide in buffered solutions at pH's 7.0, 7.5 and 8.0 following short term exposure to commonly encountered storage conditions (i.e. −20° C., 2° C.-8° C., 25° C., and 40° C.) at a solution concentration of 8 mg/mL of furosemide. No decrease in furosemide concentration was observed over 48 hours. All pH values were within 0.1 units of the initial value. Additionally, the osmolality was consistent over 48 hours. These results suggest that the Tris-buffered furosemide solutions may not be susceptible to cold-induced precipitation, as has been observed for the commercially available product.

Because 8 mg/mL furosemide solutions can be a suitable concentration for a commercial pharmaceutical product, further studies were conducted using this concentration of furosemide. Nevertheless, the results with the 8 mg/mL furosemide solutions could apply equally to other concentrations of furosemide provided the pharmaceutical formulations are in accordance with the present teachings.

Example 5 evaluated the chemical stability of 8 mg/mL furosemide in 25 mM, 50 mM, and 100 mM Tris-buffered, isosmotic solutions at pH's 7.0, 7.4 and 8.0 following three months of exposure to temperatures of −20° C., 2° C. −8° C., 25° C., and 40° C. After three months of storage, no change in furosemide concentration, pH, osmolality, or visual appearance was observed in any of the samples. FIG. 1 shows a representative HPLC chromatogram of samples of 8 mg/mL furosemide in 50 mM Tris-buffered, isosmotic solutions stored at the various temperatures for three months. The lower trace in FIG. 1 is the a diluent blank and the upper trace shows the retention time of furosemide to be about 11 minutes. These results suggest that the long term storage of the pharmaceutical formulations of the present teachings can be satisfactory for a commercial product.

Example 6 evaluated the chemical stability of 8 mg/mL furosemide in 25 mM, 50 mM, and 100 mM Tris-buffered, isosmotic solutions at pH's 7.0, 7.4, and 8.0 following three month exposure to accelerated storage conditions (i.e., 70° C.). Accelerated storage conditions attempt to advance any deleterious effects that would result upon long term exposure of the solutions to commonly encountered storage conditions. The aggressive storage conditions can be used to identify trends in the results to inform early-on of possible direction for development of commercial products.

In particular, isosmotic solutions containing 8 mg/mL furosemide with concentrations of Tris of 25 mM, 50 mM, and 100 mM and at pH's 7.0, 7.4, and 8.0 were subjected to 70° C. over three months. After 3 months at 70° C., furosemide concentration and pH decreased significantly, and osmolality slightly increased. FIGS. 2A-2C, 3A-3C and 4A-4C show the trends of the results more dramatically. In particular, a significant furosemide degradation product can be seen in the HPLC chromatograms at a retention time of about five minutes. Moreover, in FIGS. 4A-4C, which are the 25 mM Tris-buffered samples, other degradation products can be seen as double peaks at a retention time between about 7 to 7.5 minutes. As confirmed by the analytical measurement of the concentration of furosemide in the solutions, the trends of the results show that at lower pH and at lower concentrations of Tris, the stability of the solutions is reduced.

Indeed the results show a trend which suggests that a molar excess of Tris to furosemide can be advantageous for the stability of the solution. An 8 mg/mL furosemide solution having a concentration of 25 mM Tris has a Tris:furosemide ratio of about 1:1. When the concentration of Tris is 50 mM, a solution containing 8 mg/mL furosemide would have a Tris:furosemide ratio of about 2:1. Accordingly, the trend of the results of Example 6 suggests that a higher molar ratio of Tris to furosemide can improve the stability of the liquid pharmaceutical formulations. For example, a pharmaceutical formulation can include a molar ratio of Tris:furosemide of greater than or equal to about 1.25, greater than or equal to about 1.5, greater than or equal to about 1.65, greater than or equal to about 2, greater than or equal to about 2.5, or greater than or equal to about 3, which can improve the stability and other beneficial characteristics of the pharmaceutical formulation.

The trends of the results also suggest a pH dependency. In particular, the results suggest that a non-acidic pH can improve the stability of the liquid pharmaceutical formulations. For example, a pharmaceutical formulation can have a pH greater than about 7.2, greater than about 7.3, or greater than about 7.4, which can improve the stability of the formulation while also remaining near physiological pH. Although the higher end of the pH range to about 8.5 to about 9 can be advantageous for stability and solubility, a high end of the pH range of about 8 (or lower) is closer to physiological pH and can be advantageous for that purpose.

Consequently, the results and their trends suggest that a pharmaceutical formulation having a concentration of Tris is greater than or equal to about 50 mM, a molar excess of Tris to furosemide, and within a pH-1 range of about 7 to about 8.5 can provide a stable, liquid pharmaceutical formulation suitable for subcutaneous administration.

Qualitative observations were made with respect to the stability of 8 mg/mL of furosemide in 25 mM, 50 mM, and 100 mM Tris-buffered, isosmotic solutions in a pH range of 7-8 after short term exposure to light. Visual inspection of the vials after light exposure showed a dark brown colored solution for the solution containing 25 mM Tris, with progressively lighter shades of brown for the 50 mM and 100 mM Tris-buffered solutions, respectively. These qualitative results correlate well with the results of the accelerated storage conditions of Example 6.

Example 7 evaluated the dry heat sterilization of 8 mg/mL furosemide at pH 7.4 in 100 mM and 50 mM Tris-buffered solutions that were previously stored at 2° C.-8° C. for 1 month. The results suggest that heat sterilization can be a feasible approach for the terminal sterilization of a pharmaceutical formulation of the present teachings.

Furosemide, therapeutic combinations, and pharmaceutical formulations of the present teachings can be useful for treating a pathological condition or disorder in a patient, for example, a human. As used herein, "treating" refers to partially or completely alleviating and/or ameliorating the condition and/or symptoms thereof. The present teachings accordingly include a method of providing to a patient a pharmaceutical composition that includes a compound or therapeutic combination of the present teachings in combination or association with a pharmaceutically acceptable carrier. Compounds and therapeutic combinations of the present teachings can be administered alone or in combination with other therapeutically effective compounds or therapies for the treatment of a pathological condition or disorder.

As used herein, "therapeutically effective" refers to a substance or an amount that elicits a desirable biological activity or effect.

The pharmaceutical formulations of the present teachings can be sterile solutions or suspensions. A sterile pharmaceutical formulation can be prepared using pharmaceutically accepted practices, for example, filtration and/or heat.

The pharmaceutical formulations can be administered parenterally, including by infusion, injection or implantation, which includes subcutaneous administration as appropriate. For example, the pharmaceutical formulations can be administered by, for example, subcutaneous injection or delivery, or intravenous injection or delivery.

A number of devices have been proposed to facilitate self-administration of a pharmaceutical formulation. The device typically includes a reservoir containing, for example, pre-loaded with, the pharmaceutical formulation to be administered. For example, a micropump can provide precise subcutaneous administration of small quantities of a liquid pharmaceutical formulation. Such micropumps can be compact and portable. Another type of device useful for subcutaneous delivery or administration of pharmaceutical formulations is often referred to as a patch device or a pump-patch device. Patch devices usually are attached directly to the skin of a patient. See, e.g., U.S. Pat. Nos. 8,282,366 and 8,414,532 to Sensile Pat AG.

Accordingly, in various embodiments, a medical device such as a micropump or patch device can include a reservoir containing a pharmaceutical formulation, a subcutaneous injection needle configured for removable insertion into skin of a patient, a micropump having an inlet in fluid communication with the reservoir and an outlet in fluid communication with the subcutaneous injection needle, a control system configured for controlling the micropump to deliver the pharmaceutical formulation from the reservoir to the subcutaneous injection needle, whereby the pharmaceutical formulation is administered subcutaneously to a patient, and a housing for supporting the reservoir, subcutaneous injection needle, micropump and control system, the housing being portable and adapted for contact with the skin of the patient. The pharmaceutical formulation contained within the reservoir can be any of the pharmaceutical formulation of the present teachings, for example, a pharmaceutical formulation comprising between about 6 mg/mL to about 10 mg/mL of furosemide, or a pharmaceutically acceptable salt, hydrate or ester thereof, and a pharmaceutically acceptable buffer comprising tris(hydroxymethyl)aminomethane at a concentration of greater than or equal to about 50 mM, the molar ratio of tris(hydroxymethyl)aminomethane to furosemide being greater than or equal to 1.65, the pharmaceutical formulation having a pH between about 7.2 to about 8 and being isosmotic.

In certain embodiments, the medical device can be of a unitary construction. Such medical devices can be for a single or one-time use. In particular embodiments, the medical device can be of a multi-piece construction. In such medical devices, a disposable or a reuseable portion or component can be present. For example, a housing defining or including the reservoir can be a disposable or a reuseable component of the medical device. In some embodiments, the disposable or reuseable housing defining or including the reservoir can contain a pharmaceutical formulation of the present teachings. In various embodiments, the subcutaneous injection needle can be a disposable component of the medical device.

When administered for the treatment or inhibition of a particular disease state, condition or disorder, it is understood that an effective dosage can vary depending upon many factors such as the particular compound or therapeutic combination utilized, the mode of administration, and severity of the condition being treated, as well as the various physical factors related to the individual being treated. In therapeutic applications, a compound or therapeutic combination of the present teachings can be provided to a patient already suffering from a disease, for example, bacterial infection, in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

The compounds and therapeutic combinations described herein can be administered parenterally. Solutions or suspensions of these active compounds or pharmaceutically acceptable salts, hydrates, or esters thereof can be prepared in water suitably mixed with a surfactant such as hydroxylpropylcellulose. Dispersions can also be prepared in glycerol, liquid polyethylene glycols, and mixtures thereof in oils. Examples of liquid carriers for parenteral administration include water, alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration.

In certain embodiments, a parenteral preparation can include a preservative to inhibit the growth of microorganisms. However, in some embodiments, the parenteral preparation is preservative-free. In particular embodiments, a parenteral preparation can include a buffer as well as other suitable pharmaceutical additives mentioned herein such as solubilizers, emulsifiers, preservatives, sweeteners, flavoring agents, suspending agents, thickening agents, colors, viscosity regulators, stabilizers, and osmo-regulators.

The pharmaceutical forms suitable for injection can include sterile aqueous solutions or dispersions and sterile powders for the extemporaneous preparation of sterile injectable solutions or dispersions. In certain embodiments, the pharmaceutical form is sterile and its viscosity permits it to flow through a syringe. The pharmaceutical form should be stable under the conditions of manufacture and storage, for example, preserved against the contaminating action of microorganisms such as bacteria and fungi, if needed. The carrier can be a solvent or dispersion medium containing liquids such as water, ethanol, polyol (e.g., glycerol, propylene glycol, and liquid polyethylene glycol), suitable mixtures thereof, and vegetable oils.

Although the present teachings can provide methods and pharmaceutical formulations that can achieve one or more of the desired characteristics for subcutaneous administration of furosemide, certain of the characteristics of the pharmaceutical formulations, for example, being at or near physiological pH and/or being isosmotic or substantially isosmotic, also can be desirable for intravenous and other types of parenteral administration to a patient and are within the scope of the present teachings.

The following examples are provided to illustrate further and to facilitate the understanding of the present teachings and are not in any way intended to limit the invention.

EXAMPLES

The materials, equipment, and procedures for the examples were as follows.

Materials

| Material | Manufacturer or Supplier | Part # | Lot # or Serial # |
|---|---|---|---|
| Furosemide | Alfa Aesar | J61457 | J04Y011 |
| Formic acid | J. T. Baker | 0128-01 | G20J03 |
| Methanol | EMD | MX0475-1 | 52180 |
| Sodium phosphate, monobasic | Spectrum | SO187 | VK1125 |
| Sodium phosphate, dibasic | Spectrum | SO138 | WG0695 |
| Sodium phosphate, tribasic | EMD | SX0725-1 | 3031C517 |
| 0.5M Potassium phosphate, pH 7.4 | BD Gentest | — | 6123 |
| Trizma pre-set crystals, pH 7.5 | Sigma | T7818 | 108K5435 |
| Trizma pre-set crystals, pH 8.5 | Sigma | T8818 | 079K5414 |
| Tris base | G. Biosciences | RC-105 | 081006 |
| Tris HCl | Sigma | T-5941 | 111K5405 |
| Hydrochloric acid | Ricca | 3770-16 | 2101466 |
| Syringe | BD | 309653 | 7130051 |
| 0.2 µm nylon syringe filter | Pall | 4433 | 22361 |
| 0.45 µm nylon filters | Pall | 66608 | T115491 |
| Water | In-house deionized (Barnstead Nanopure) | | |

For Examples 5-7, the following changes are noted with respect to the materials.

| Material | Manufacturer or Supplier | Part # | Lot # or Serial # |
|---|---|---|---|
| Furosemide | scPharma | — | 2094HRII, 2089HRII, 2093HRII |
| Methanol | EMD | MX0475-1 | 53003 |
| Tris base | J. T. Baker | 4102-01 | 0000033772 |
| Tris HCl | J. T. Baker | 4106-01 | 0000039560 |
| Sodium hydroxide pellets | EMD | SX0600-1 | B0806662 |
| Hydrochloric acid | Macron | 2612-14 | 0000035974 |
| Sodium chloride | EMD | 1.06400.1003 | K93181300 |
| 0.2 µm nylon filters | Pall | 66602 | T11621 |
| Water | In-house deionized (Barnstead Nanopure) | | |

Equipment

| Equipment | Description | |
|---|---|---|
| HPLC System (WLI HPLC #12) | Chromatograph: | Shimadzu Prominence LC-20 AT |
| | Detector: | Shimadzu Prominence SPD-20A |
| | Software System: | Shimadzu Class VP Software |
| Analytical balances | Mettler Toledo MX-5 Mettler Toledo AB204/S-FACT | |
| pH meter | Orion 4 Star Plus pH and conductivity meter pH electrode (VWR Symphony) Automatic temperature compensation probe (Thermo) | |
| Osmometer | Precision Systems μOsmette | |

Procedures

1. Preparation of Phosphate Buffers 100 mM monobasic sodium phosphate: A quantity of 24.0 g of anhydrous monobasic sodium m phosphate was accurately weighed on an analytical balance, dispensed into a 2 L volumetric flask, and dissolved in DI water. The flask was filled to volume with water and inverted to mix thoroughly. The pH of the resulting solution was 4.55.

100 mM dibasic sodium phosphate: A quantity of 28.4 g of anhydrous dibasic sodium phosphate was accurately weighed on an analytical balance, dispensed into a 2 L volumetric flask, and dissolved in DI water. The flask was filled to volume with water and inverted to mix thoroughly. The pH of the resulting solution was 9.20.

100 mM tribasic sodium phosphate: A quantity of 3.8 g of tribasic sodium phosphate, dodecahydrate was accurately weighed on an analytical balance, dispensed into a 100 mL volumetric flask, and dissolved in DI water. The flask was filled to volume with water and inverted to mix thoroughly. The pH of the resulting solution was 12.32.

Solutions of 100 mM phosphate were prepared by combining the component solutions in appropriate volumes to produce buffers of pH 7.0, 7.2, and 7.5-8.5 in 0.1 unit increments.

2. Preparation of Tris Buffers 200 mM Tris HCl: A quantity of 15.8 g of Tris HCl was accurately weighed on an analytical balance, dispensed into a 500 mL volumetric flask, and dissolved in DI water. The flask was filled to volume with water and inverted to mix thoroughly. The pH of the resulting solution was 4.45.

200 Tris base: A quantity of 12.1 g of Tris base was accurately weighed on an analytical balance, dispensed into a 500 mL volumetric flask, and dissolved in DI water. The flask was filled to volume with water and inverted to mix thoroughly. The pH of the resulting solution was 10.60.

Solutions of 200 mM Tris were prepared by combining the component solutions in appropriate volumes to produce buffers of pH 6.7, 6.9, 7.1-7.7 in 0.1 unit increments, 7.9, 8.1, 8.3 and 8.5.

3. Preparation of 0.1 mg/mL Furosemide Solutions

A quantity of approximately 40 mg furosemide was dispensed into each of thirteen conical tubes and dissolved to 10 mg/mL in the appropriate volume of 100 mM dibasic sodium phosphate or the buffer of desired target pH. The resulting solutions were adjusted to the target pH values of 7.0, 7.2, and 7.5-8.5, in 0.1 unit increments, using 100 mM monobasic, dibasic, or tribasic sodium phosphate, as necessary. All solutions were diluted to 0.1 mg/mL furosemide using the appropriate pH buffer.

4. Preparation of 20 mg/mL Furosemide Solutions

A quantity of approximately 100 mg furosemide was dispensed into each of thirteen conical tubes and dissolved to 40 mg/mL in the appropriate volume of 200 mM Tris base or a sufficiently high pH buffer (i.e. greater than pH 8.0). The resulting solutions were adjusted to the target pH values of 6.7, 6.9, 7.1-7.7 in 0.1 unit increments, 7.9, 8.1, 8.3 and 8.5, using 200 mM Tris HCl or 1 N hydrochloric acid, as necessary. Specifically, addition of HCl was required to achieve pH values of 6.7 and 6.9. All solutions were diluted to 20 mg/mL furosemide using the appropriate pH buffer.

5. Preparation of 8 mg/mL Furosemide Solutions

A quantity of approximately 200 mg furosemide was dispensed into each of three conical tubes and dissolved to 20 mg/mL in the appropriate volume of 200 mM Tris base. The resulting solutions were adjusted to the target pH values of 7.0, 7.5, and 8.0, using 200 mM Tris HCl or 1 N hydrochloric acid, as necessary. Specifically, addition of HCl was required to achieve a pH value of 7.0. All solutions were diluted to a final target concentration of 8 mg/mL furosemide using the appropriate pH buffer. Upon preparation, samples were filtered through 0.2 μm nylon filters.

6. Measurement of Solution Osmolality

The osmolality values of 50 μL aliquots of each sample were measured by freezing point depression.

7. Preparation of Mobile Phases

Mobile phase A, 0.1% formic acid in water: A volume of approximately 1900 mL of deionized water was dispensed into a 2 L volumetric flask. After adding 2 mL of formic acid, the flask was brought to volume with water and inverted several times to mix thoroughly. The resultant solution was filtered through a 0.45 μm nylon filter.

Mobile phase B, 0.1% formic acid in methanol: A volume of approximately 1900 mL of methanol was dispensed into a 2 L volumetric flask. After adding 2 mL of formic acid, the flask was brought to volume with methanol and inverted several times to mix thoroughly. The resultant solution was filtered through a 0.45 μm nylon filter.

8. Preparation of Linearity Standards for HPLC

A quantity of 5 mg of furosemide was accurately weighed on an analytical balance and dispensed into a 5 mL volumetric flask. The solid was dissolved and the flask filled to volume with methanol diluent to produce a 1 mg/mL stock solution. Linearity standards were prepared from the stock solution as described in the table below.

| Standard # | Volume of stock (μL) | Volume of diluent (μL) | Nomial [API] (mg/mL) |
|---|---|---|---|
| L1 | 2 | 998 | 0.002 |
| L2 | 5 | 995 | 0.005 |
| L3 | 10 | 990 | 0.010 |
| L4 | 50 | 950 | 0.050 |
| L5 | 100 | 900 | 0.100 |
| L6 | 150 | 850 | 0.150 |

Example 1

Unbuffered Furosemide Studies

A study was conducted to determine the appropriate ratio of HCl to furosemide to produce aqueous solutions in a target pH range of 7.5 to 8.5. Nine samples were prepared by dispensing 80 mg of furosemide each into nine tubes. An excess of sodium hydroxide was added to each tube, corresponding to 2.48 μmoles base per 1 μmole of furosemide, to ensure complete dissolution was obtained upon addition of saline. An appropriate volume of saline was added to the resulting solution targeting a concentration of 8 mg/mL. Various volumes of 10 N hydrochloric acid ("HCl") were added to each sample to attempt to obtain solutions of pH 7.5 to 8.5. The results of the study are summarized in Table 1 below.

TABLE 1

Summary of results.

| Sample | HCl/API, (μmole/μmole) | pH | Visual Assessment |
|---|---|---|---|
| 1 | 1.462 | 8.8 | Clear solution |
| 2 | 1.498 | 5.8 | Clear solution |
| 3 | 1.508 | 8.5 | Clear solution |
| 4 | 1.515 | 8.4 | Clear solution |
| 5 | 1.518 | 6.1 | Solids present |
| 6 | 1.528 | 6.0 | Solids present |
| 7 | 1.531 | 6.0 | Solids present |
| 8 | 1.535 | 5.8 | Solids present |
| 9 | 1.538 | 6.0 | Solids present |

Clear solutions within the targeted pH range of 7.5 to 8.5 were achieved in samples 3 and 4 only, which are at the top of the desired range. Additionally, it was observed that very small changes in the quantity of acid added resulted in precipitation of solids and a disproportionate decrease in pH, as demonstrated by the difference in pH between samples 4 and 5. These results suggest that the preparation of unbuffered furosemide solutions at the low end of the desired pH range is likely unfeasible due to the highly variable pH values obtained following addition of very similar molar equivalents of acid.

Example 2

Buffered Furosemide Studies

A study was conducted to determine whether a buffer would improve the pH stability of furosemide in the pH range of 7 to 8.5 and what buffer strength was necessary to maintain a nominal pH upon preparation of a saturated furosemide solution. Accordingly, sodium phosphate buffer, potassium phosphate buffer, and Tris buffer systems were evaluated at pH values in the target range of 7.0 to 8.5 and at selected buffer concentrations ranging from 150 mM to 500 mM.

Samples were prepared such that complete dissolution, though not anticipated, would result in a target concentration of approximately 30 mg/mL furosemide and measured for pH immediately following preparation. The results are summarized in the Table 2 below.

TABLE 2

Summary of results at time zero ($t_0$).

| Sample # | Target pH | Buffer Strength (mM) | pH | Visual Observation |
|---|---|---|---|---|
| Sodium Phosphate Buffer | | | | |
| 1 | 7.5 | 500 | — | "Gel" with clumps |
| 2 | | 400 | — | Solution with clumps |
| 3 | | 300 | — | Solution with clumps |
| 4 | | 200 | 6.93 | Suspension with fine solids |
| 5 | | 100 | 6.88 | Suspension with fine solids |
| 6 | 8.5 | 500 | — | "Gel" with clumps |
| 7 | | 400 | — | Solution with clumps |
| 8 | | 300 | — | Solution with clumps |
| 9 | | 200 | 6.99 | Suspension with fine solids |
| 10 | | 100 | 6.97 | Suspension with fine solids |

TABLE 2-continued

Summary of results at time zero ($t_0$).

| Sample # | Target pH | Buffer Strength (mM) | pH | Visual Observation |
|---|---|---|---|---|
| Potassium Phosphate Buffer | | | | |
| 1 | 7.4 | 500 | 7.05 | Solution with clumps |
| 2 | | 400 | 6.99 | Solution with needles |
| 3 | | 300 | 7.02 | Suspension with fine solids |
| Tris Buffer | | | | |
| 1 | 7.5 | 500 | 7.21 | Visually dissolved solutions |
| 2 | 8.5 | 500 | 8.25 | Visually dissolved solutions |

After 24 hours at ambient conditions, samples were centrifuged to pellet any undissolved solids and the resulting supernatant was measured for pH and concentration by HPLC. The results are summarized in Table 3 below.

TABLE 3

Summary of results after 24 hours.

| Sample # | Target pH | Buffer Strength (mM) | Ionic Strength (mM)[1] | pH | [Furosemide], mg/mL |
|---|---|---|---|---|---|
| Sodium Phosphate Buffer | | | | | |
| 1 | 7.5 | 500 | 1161 | 6.98 | 5.81 |
| 2 | | 400 | 929 | 6.90 | 7.99 |
| 3 | | 300 | 697 | 6.86 | 10.6 |
| 4 | | 200 | 464 | 6.94 | 15.2 |
| 5 | | 150 | 348 | 6.90 | 14.3 |
| 6 | 8.5 | 500 | 1161 | 7.27 | 5.7 |
| 7 | | 400 | 929 | 7.22 | 7.82 |
| 8 | | 300 | 697 | 6.97 | 12.9 |
| 9 | | 200 | 464 | 6.95 | 16.1 |
| 10 | | 150 | 348 | 6.96 | 18.4 |
| Potassium Phosphate Buffer | | | | | |
| 1 | 7.4 | 500 | 1161 | 7.06 | 10.3 |
| 2 | | 400 | 929 | 6.99 | 13.7 |
| 3 | | 300 | 697 | 7.02 | 18.7 |
| Tris Buffer | | | | | |
| 1 | 7.5 | 500 | 394 | 7.26 | 31.9 |
| 2 | 8.5 | 500 | 135 | 8.33 | 32.2 |

[1]Ionic strength calculated for buffers at target pH prior to addition of furosemide.

The results suggest that both the buffer identity and strength have a significant effect on the resulting solution concentration. With respect to the phosphate buffer systems, a trend was observed such that reducing the buffer strength resulted in a corresponding increase in furosemide solubility. The trend appears to correlate with the ionic strength of the buffer solutions.

The Tris buffer system was observed to maintain solution pH values that were closer to the nominal values than the various phosphate buffer systems evaluated even though the solution concentration of furosemide was significantly higher in the Tris solutions. More specifically, the results suggested that solution concentrations of up to approximately 32 mg/mL of furosemide could be achieved. Additionally, the pH 7.5 Tris solution was capable of maintaining significantly higher solution concentrations than phosphate buffer solutions at comparable pH and ionic strength.

Example 3

Buffered Furosemide Studies—pH Range

A study was conducted to evaluate the chemical and physical stability of 20 mg/mL furosemide Tris-buffered solutions over a pH range of 6.7 to 8.5 at ambient temperature. Although the results in Example 2 suggested that solution concentrations of about 32 mg/mL of furosemide could be attained and that these samples were not saturated at this concentration, a lower concentration that may be more appropriate for a pharmaceutical formulation was selected for evaluation.

A quantity of approximately 100 mg furosemide was dispensed into each of thirteen conical tubes and dissolved to 40 mg/mL in the appropriate volume of 200 mM Tris base or a 200 mM Tris buffer having a pH between 8 to 8.5. The resulting solutions were adjusted to the target pH values of 6.7, 6.9, 7.1 to 7.7 in 0.1 unit increments, 7.9, 8.1, 8.3 and 8.5, using 200 mM Tris HCl or 1 N HCl, as necessary. All solutions were diluted to 20 mg/mL of furosemide using the appropriate pH buffer. Upon preparation, samples were analyzed for concentration and purity by HPLC and for pH. Samples were stored at ambient temperature and subsequently analyzed after 24 and 48 hours of storage. The concentrations and pH values are summarized in Table 4 and Table 5, respectively.

TABLE 4

Summary of furosemide concentrations over 48 hours.

| | | Furosemide Concentration (mg/mL) | | |
|---|---|---|---|---|
| Sample # | Nominal pH | $t_0$ | t = 24 h | t = 48 h |
| 1 | 6.7 | 20.0 | 21.0 | 21.2 |
| 2 | 6.9 | 20.6 | 20.8 | 21.0 |
| 3 | 7.1 | 20.8 | 20.5 | 20.8 |
| 4 | 7.2 | 20.7 | 20.6 | 21.0 |
| 5 | 7.3 | 20.6 | 20.6 | 19.9 |
| 6 | 7.4 | 21.0 | 20.6 | 20.5 |
| 7 | 7.5 | 20.6 | 20.5 | 20.2 |
| 8 | 7.6 | 20.1 | 20.7 | 20.6 |
| 9 | 7.7 | 20.2 | 20.7 | 20.1 |
| 10 | 7.9 | 20.4 | 20.4 | 20.4 |
| 11 | 8.1 | 20.2 | 19.4 | 20.5 |
| 12 | 8.3 | 20.0 | 20.0 | 20.3 |
| 13 | 8.5 | 20.2 | 20.8 | 20.5 |

TABLE 5

Summary of solution pH over 48 hours.

| | | Furosemide pH | | |
|---|---|---|---|---|
| Sample # | Nominal pH | $t_0$ | t = 24 h | t = 48 h |
| 1 | 6.7 | 6.66 | 6.67 | 6.75 |
| 2 | 6.9 | 6.92 | 6.91 | 6.98 |
| 3 | 7.1 | 7.12 | 7.08 | 7.17 |
| 4 | 7.2 | 7.21 | 7.20 | 7.27 |
| 5 | 7.3 | 7.27 | 7.27 | 7.36 |
| 6 | 7.4 | 7.38 | 7.36 | 7.45 |
| 7 | 7.5 | 7.51 | 7.47 | 7.57 |
| 8 | 7.6 | 7.62 | 7.59 | 7.65 |
| 9 | 7.7 | 7.69 | 7.64 | 7.73 |
| 10 | 7.9 | 7.87 | 7.83 | 7.93 |
| 11 | 8.1 | 8.11 | 8.04 | 8.14 |
| 12 | 8.3 | 8.29 | 8.28 | 8.37 |
| 13 | 8.5 | 8.48 | 8.48 | 8.57 |

No decrease in sample concentration was observed over 48 hours. All pH values were within 0.1 units of the initial value.

Example 4

Buffered Furosemide Studies—Short Term Storage Conditions

A study was conducted to evaluate the chemical and physical stability of furosemide in Tris-buffered solutions at pH's 7.0, 7.5, and 8.0 following short term exposure to commonly encountered storage conditions (i.e., −20° C., 2° C.-8° C., 25° C., and 40° C.). A quantity of approximately 200 mg furosemide was dispensed into each of three conical tubes and dissolved to 20 mg/mL in the appropriate volume of 200 mM Tris base. The resulting solutions were adjusted to the target pH values of 7.0, 7.5, and 8.0, using 200 mM Tris-HCl or 1 N HCl, as necessary. All solutions were diluted to a final target concentration of 8 mg/mL furosemide using the appropriate pH buffer. Upon preparation, samples were filtered through 0.2 µm nylon filters and analyzed for concentration and purity by HPLC, and for pH and osmolality. Aliquots of each sample were stored at each condition and subsequently filtered and analyzed after 24 and 48 hours of storage. The results are summarized in Tables 6-8 below.

TABLE 6

Summary of furosemide concentrations over 48 hours.

| | | | Furosemide Concentration (mg/mL) | | |
|---|---|---|---|---|---|
| Sample # | Nominal pH | Condition | $t_0$ | t = 24 h | t = 48 h |
| 1 | 7.0 | −20° C. | 8.59 | 8.38 | 8.53 |
| | | 2-8° C. | | 8.42 | 8.72 |
| | | 25° C. | | 8.52 | 8.44 |
| | | 40° C. | | 8.41 | 8.51 |
| 2 | 7.5 | −20° C. | 8.75 | 10.1* | 8.47 |
| | | 2-8° C. | | 8.50 | 8.37 |
| | | 25° C. | | 8.39 | 8.48 |
| | | 40° C. | | 8.49 | 8.45 |
| 3 | 8.0 | −20° C. | 8.70 | 8.49 | 8.49 |
| | | 2-8° C. | | 8.47 | 8.56 |
| | | 25° C. | | 8.42 | 8.65 |
| | | 40° C. | | 8.55 | 8.44 |

*Outlier sample concentration, likely due to dilution error.

TABLE 7

Summary of solution pH over 48 hours.

| | | | Furosemide pH | | |
|---|---|---|---|---|---|
| Sample # | Nominal pH | Condition | $t_0$ | t = 24 h | t = 48 h |
| 1 | 7.0 | −20° C. | 6.95 | 6.99 | 6.99 |
| | | 2-8° C. | | 6.98 | 6.98 |
| | | 25° C. | | 6.97 | 7.01 |
| | | 40° C. | | 6.97 | 7.01 |
| 2 | 7.5 | −20° C. | 7.48 | 7.53 | 7.54 |
| | | 2-8° C. | | 7.52 | 7.55 |
| | | 25° C. | | 7.52 | 7.55 |
| | | 40° C. | | 7.53 | 7.56 |
| 3 | 8.0 | −20° C. | 7.92 | 7.96 | 7.97 |
| | | 2-8° C. | | 7.96 | 8.00 |
| | | 25° C. | | 7.96 | 8.02 |
| | | 40° C. | | 7.97 | 8.00 |

TABLE 8

Summary of solution osmolality over 48 hours.

| | | | Furosemide Osmolality (mOsm/kg $H_2O$) | | |
|---|---|---|---|---|---|
| Sample # | Nominal pH | Condition | $t_0$ | t = 24 h | t = 48 h |
| 1 | 7.0 | 25° C. | 342 | 343 | 346 |
| 2 | 7.5 | | 339 | 340 | 341 |
| 3 | 8.0 | | 305 | 308 | 308 |

No decrease in furosemide concentration was observed over 48 hours. All pH values were within 0.1 units of the initial value. Additionally, the osmolality of the solutions was consistent over 48 hours. These results suggest that the Tris buffered furosemide solutions may not be susceptible to cold-induced precipitation, as has been observed for the commercially available product.

Example 5

Buffered Furosemide Studies—Longer Term Storage Conditions

A longer term stability study was conducted to evaluate the chemical stability of 8 mg/mL furosemide in Tris-buffered (25 mM, 50 mM, and 100 mM), isosmotic solutions at pH's 7.0, 7.4, and 8.0 upon storage at temperatures of −20° C., 2° C.-8° C., 25° C., and 40° C. After three months of storage, samples were removed from their respective storage conditions and equilibrated to room temperature, filtered, and the supernatant tested for concentration and purity by HPLC, and for pH and osmolality. The results are summarized in Tables 9-11 below and generally in FIG. 1.

TABLE 9

Summary of analysis in 100 mM Tris.

| Storage Condition | Nominal pH | [Furosemide], mg/mL | pH | Osmolality, mOsm/kg $H_2O$ |
|---|---|---|---|---|
| $t_0$ | 8.0 | 8.08 | 7.99 | 292 |
| | 7.4 | 8.17 | 7.42 | 297 |
| | 7.0 | 8.04 | 7.02 | 292 |
| −20° C. | 8.0 | 7.89 | 7.99 | 296 |
| | 7.4 | 7.92 | 7.42 | 301 |
| | 7.0 | 7.90 | 7.00 | 298 |
| 2-8° C. | 8.0 | 7.91 | 7.99 | 295 |
| | 7.4 | 7.95 | 7.41 | 301 |
| | 7.0 | 7.89 | 7.00 | 296 |
| 25° C. | 8.0 | 7.79 | 7.97 | 288 |
| | 7.4 | 7.82 | 7.41 | 295 |
| | 7.0 | 7.79 | 6.99 | 293 |
| 40° C. | 8.0 | 7.79 | 7.98 | 294 |
| | 7.4 | 7.90 | 7.39 | 297 |
| | 7.0 | 7.87 | 6.98 | 294 |

TABLE 10

Summary of analysis in 50 mM Tris.

| Storage Condition | Nominal pH | [Furosemide], mg/mL | pH | Osmolality, mOsm/kg $H_2O$ |
|---|---|---|---|---|
| $t_0$ | 8.0 | 8.14 | 8.04 | 288 |
| | 7.4 | 8.09 | 7.44 | 289 |
| | 7.0 | 8.06 | 7.04 | 290 |
| −20° C. | 8.0 | 7.93 | 8.11 | 289 |
| | 7.4 | 7.93 | 7.52 | 292 |
| | 7.0 | 8.12 | 7.13 | 289 |
| 2-8° C. | 8.0 | 7.84 | 8.10 | 296 |
| | 7.4 | 8.10 | 7.50 | 293 |
| | 7.0 | 8.02 | 7.10 | 294 |
| 25° C. | 8.0 | 7.82 | 8.09 | 296 |
| | 7.4 | 7.87 | 7.49 | 292 |
| | 7.0 | 8.07 | 7.10 | 290 |
| 40° C. | 8.0 | 7.95 | 8.10 | 289 |
| | 7.4 | 7.97 | 7.50 | 296 |
| | 7.0 | 7.94 | 7.12 | 295 |

TABLE 11

Summary of analysis in 25 mM Tris.

| Storage Condition | Nominal pH | [Furosemide], mg/mL | pH | Osmolality, mOsm/kg $H_2O$ |
|---|---|---|---|---|
| $t_0$ | 8.0 | 8.08 | 8.04 | 289 |
| | 7.4 | 8.00 | 7.42 | 287 |
| | 7.0 | 8.09 | 7.02 | 293 |
| −20° C. | 8.0 | 7.91 | 8.06 | 291 |
| | 7.4 | 7.92 | 7.47 | 288 |
| | 7.0 | 7.91 | 7.07 | 296 |
| 2-8° C. | 8.0 | 7.97 | 8.07 | 292 |
| | 7.4 | 7.79 | 7.49 | 291 |
| | 7.0 | 8.01 | 7.06 | 297 |
| 25° C. | 8.0 | 7.76 | 8.06 | 294 |
| | 7.4 | 7.81 | 7.47 | 289 |
| | 7.0 | 7.91 | 7.09 | 298 |
| 40° C. | 8.0 | 7.99 | 8.07 | 294 |
| | 7.4 | 7.90 | 7.47 | 290 |
| | 7.0 | 7.89 | 7.08 | 296 |

After three months of storage, no change in furosemide concentration, pH, osmolality, or visual appearance was observed in any of the samples.

Example 6

Buffered Furosemide Studies—Accelerated Storage Conditions

A study was conducted to evaluate the chemical stability of 8 mg/mL furosemide in Tris-buffered (25 mM, 50 mM, and 100 mM), isosmotic solutions at pH's 7.0, 7.4, and 8.0 upon storage at a temperature of 70° C. After three months of storage, samples were removed from the storage conditions and equilibrated to room temperature, filtered, and the supernatant tested for concentration and purity by HPLC, and for pH and osmolality. The results are summarized in Tables 12-14 below and in FIGS. 2A-2C, 3A-3C, and 4A-4C.

TABLE 12

Summary of analysis in 100 mM Tris.

| Storage Condition | Nominal pH | [Furosemide], mg/mL | pH | Osmolality, mOsm/kg $H_2O$ |
|---|---|---|---|---|
| $t_0$ | 8.0 | 8.08 | 7.99 | 292 |
| | 7.4 | 8.17 | 7.42 | 297 |
| | 7.0 | 8.04 | 7.02 | 292 |
| 70° C. | 8.0 | 3.67 | 7.56 | 303 |
| | 7.4 | 0.58 | 5.68 | 312 |
| | 7.0 | <0.002 | 4.54 | 306 |

TABLE 13

Summary of analysis in 50 mM Tris.

| Storage Condition | Nominal pH | [Furosemide], mg/mL | pH | Osmolality, mOsm/kg H$_2$O |
|---|---|---|---|---|
| t$_0$ | 8.0 | 8.14 | 8.04 | 288 |
| | 7.4 | 8.09 | 7.44 | 289 |
| | 7.0 | 8.06 | 7.04 | 290 |
| 70° C. | 8.0 | 3.60 | 7.30 | 311 |
| | 7.4 | <0.002 | 4.73 | 311 |
| | 7.0 | <0.002 | 4.50 | 305 |

TABLE 14

Summary of analysis in 25 mM Tris.

| Storage Condition | Nominal pH | [Furosemide], mg/mL | pH | Osmolality, mOsm/kg H$_2$O |
|---|---|---|---|---|
| t$_0$ | 8.0 | 8.08 | 8.04 | 289 |
| | 7.4 | 8.00 | 7.42 | 287 |
| | 7.0 | 8.09 | 7.02 | 293 |
| 70° C. | 8.0 | 1.16 | 5.26 | 297 |
| | 7.4 | <0.002 | 4.57 | 299 |
| | 7.0 | <0.002 | 4.44 | 308 |

After 3 months of storage at 70° C., furosemide concentration and pH decreased significantly, osmolality slightly increased, and the samples were observed to be dark brown in color.

Example 7

Buffered Furosemide Studies—Heat Sterilization Conditions

A study was conducted to evaluate the dry heat sterilization of 8 mg/mL furosemide in 100 mM and 50 mM Tris-buffered solutions at pH 7.4 that were previously stored at 2° C.-8° C. for 1 month. The solutions were analyzed in triplicate for concentration and purity before and after sterilization at 120° C. for 1 hour.

TABLE 15

Summary of furosemide concentrations before and after heat sterilization.

| | Average [Furosemide], mg/mL | | |
|---|---|---|---|
| Sample Description | Before Heat Sterilization | After Heat Sterilization | % Recovery |
| 8 mg/mL, 100 mM, pH 7.4, 2° C.-8° C. | 8.16 | 7.98 | 98% |
| 8 mg/mL, 50 mM, pH 7.4, 2° C.-8° C. | 8.14 | 7.86 | 97% |

The results, summarized in Table 15 above, suggest that heat sterilization can be a feasible approach for the terminal sterilization of a pharmaceutical formulation of the present teachings.

The present teachings encompass embodiments in other specific forms without departing from the spirit or essential characteristics thereof. The foregoing embodiments are therefore to be considered in all respects illustrative rather than limiting on the present teachings described herein. Scope of the present invention is thus indicated by the appended claims rather than by the foregoing description, and all changes that come within the meaning and range of equivalency of the claims are intended to be embraced therein.

What is claimed is:

1. A method of treating a patient with or exhibiting the symptoms of edema, hypertension or heart failure, the method comprising:
    administering to a patient a liquid pharmaceutical formulation, wherein the liquid pharmaceutical formulation comprises:
        furosemide, or a pharmaceutically acceptable salt, hydrate or ester thereof, wherein furosemide is the sole therapeutically active agent in the liquid pharmaceutical formulation and the amount of furosemide in the liquid pharmaceutical formulation is between about 2 mg/mL to about 15 mg/mL; and
        a pharmaceutically acceptable buffer comprising tris(hydroxymethyl)aminomethane, wherein the concentration of tris(hydroxymethyl)aminomethane in the liquid pharmaceutical formulation is in a range of about 50 mM to about 250 mM;
    wherein the liquid pharmaceutical formulation is isosmotic and has a pH between about 7.2 to about 8, and the molar ratio of tris(hydroxymethyl)aminomethane to furosemide is greater than or equal to two.

2. The method of claim 1, wherein administering comprises administering subcutaneously the pharmaceutical formulation.

3. The method of claim 2, wherein administering subcutaneously comprises using a pump device.

4. The method of claim 3, wherein the pump device is a patch device.

5. The method of claim 1, wherein administering comprises administering intravenously the liquid pharmaceutical formulation.

6. A method of treating a patient with or exhibiting the symptoms of edema, hypertension or heart failure, the method comprising:
    administering subcutaneously to a patient a liquid pharmaceutical formulation comprising:
        furosemide, or a pharmaceutically acceptable salt, hydrate or ester thereof, wherein the liquid pharmaceutical formulation comprises about 8 mg/mL of furosemide, which is the sole therapeutically active agent; and
        a pharmaceutically acceptable buffer comprising tris(hydroxymethyl)aminomethane, wherein the concentration of tris(hydroxymethyl)aminomethane in the liquid pharmaceutical formulation is about 50 mM;
    wherein the molar ratio of tris(hydroxymethyl)aminomethane to furosemide is about 2, and the liquid pharmaceutical formulation has a pH of about 7.4 and is isosmotic.

7. The method of claim 1, wherein the amount of furosemide in the liquid pharmaceutical formulation is between about 2 mg/mL to about 10 mg/mL.

8. The method of claim 1, wherein the amount of furosemide in the liquid pharmaceutical formulation is between about 6 mg/mL to about 10 mg/mL.

9. The method of claim 6, wherein administering subcutaneously comprises using a pump device.

10. The method of claim 9, wherein the pump device is a patch device.

11. A method of treating a patient with or exhibiting the symptoms of edema, hypertension or heart failure, the method comprising:

administering subcutaneously to a patient a liquid pharmaceutical formulation, wherein the liquid pharmaceutical formulation comprises:

furosemide, or a pharmaceutically acceptable salt, hydrate or ester thereof, wherein furosemide is the sole therapeutically active agent in the liquid pharmaceutical formulation and the amount of furosemide in the liquid pharmaceutical formulation is between about 2 mg/mL to about 20 mg/mL; and a pharmaceutically acceptable buffer comprising tris(hydroxymethyl)aminomethane, wherein the concentration of tris(hydroxymethyl)aminomethane in the liquid pharmaceutical formulation is greater than or equal to about 50 mM;

wherein the liquid pharmaceutical formulation is isosmotic and has a pH between about 7 to about 8.5, and the molar ratio of tris(hydroxymethyl)aminomethane to furosemide is greater than or equal to 1.5.

12. The method of claim 11, wherein the molar ratio of tris(hydroxymethyl)aminomethane to furosemide is greater than or equal to two.

13. The method of claim 11, wherein the concentration of tris(hydroxymethyl)aminomethane in the liquid pharmaceutical formulation is in a range of about 50 mM to about 250 mM.

14. The method of claim 12, wherein the concentration of tris(hydroxymethyl)aminomethane in the liquid pharmaceutical formulation is in a range of about 50 mM to about 250 mM.

15. The method of claim 11, wherein the liquid pharmaceutical formulation has a pH between about 7.2 to about 8.

16. The method of claim 12, wherein the liquid pharmaceutical formulation has a pH between about 7.2 to about 8.

17. The method of claim 13, wherein the liquid pharmaceutical formulation has a pH between about 7.2 to about 8.

18. The method of claim 13, wherein the liquid pharmaceutical formulation has a pH between about 7.2 to about 8.

19. The method of claim 11, wherein the amount of furosemide in the liquid pharmaceutical formulation is between about 2 mg/mL to about 15 mg/mL.

20. The method of claim 12, wherein the amount of furosemide in the liquid pharmaceutical formulation is between about 2 mg/mL to about 15 mg/mL.

21. The method of claim 13, wherein the amount of furosemide in the liquid pharmaceutical formulation is between about 2 mg/mL to about 15 mg/mL.

22. The method of claim 15, wherein the amount of furosemide in the liquid pharmaceutical formulation is between about 2 mg/mL to about 15 mg/mL.

23. The method of claim 18, wherein administering subcutaneously comprises using a pump device.

* * * * *

UNITED STATES PATENT AND TRADEMARK OFFICE
CERTIFICATE OF CORRECTION

PATENT NO. : 9,884,039 B2
APPLICATION NO. : 14/781706
DATED : February 6, 2018
INVENTOR(S) : Scott A. Michaels et al.

It is certified that error appears in the above-identified patent and that said Letters Patent is hereby corrected as shown below:

On the Title Page

At Item (71) Applicant, delete "scPharmaceuticals Inc., Lexington MA (US)" and replace it with --scPharmaceuticals Inc., Burlington MA (US)--.

In the Specification

Column 1, Line 10, delete "Apr. 3, 2014, Which claims" and replace it with --Apr. 3, 2014, which claims--.

In the Claims

Claim 18, Line 1, delete "claim 13," and replace it with --claim 14,--.

Signed and Sealed this
Fourteenth Day of February, 2023

Katherine Kelly Vidal
*Director of the United States Patent and Trademark Office*